US008712507B2

(12) United States Patent
Cazares et al.

(10) Patent No.: US 8,712,507 B2
(45) Date of Patent: Apr. 29, 2014

(54) SYSTEMS AND METHODS FOR ARRANGING AND LABELING CARDIAC EPISODES

(75) Inventors: Shelley Cazares, Minneapolis, MN (US); Aaron McCabe, Minneapolis, MN (US); Alok Sathaye, Boston, MA (US); Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 248 days.

(21) Appl. No.: 11/643,220

(22) Filed: Dec. 21, 2006

(65) Prior Publication Data
US 2008/0071182 A1  Mar. 20, 2008

Related U.S. Application Data

(60) Provisional application No. 60/844,482, filed on Sep. 14, 2006.

(51) Int. Cl.
*A61B 5/04* (2006.01)

(52) U.S. Cl.
USPC ........................................................ 600/509

(58) Field of Classification Search
USPC .......... 600/508–528; 128/897, 898, 899, 905, 128/920, 922, 923
See application file for complete search history.

(56) References Cited

U.S. PATENT DOCUMENTS

| 4,550,221 A | 10/1985 | Mabusth |
| 4,686,332 A | 8/1987 | Greanias et al. |
| 4,878,497 A | 11/1989 | Callaghan et al. |
| 5,036,849 A | 8/1991 | Hauck et al. |
| 5,224,486 A * | 7/1993 | Lerman et al. ................ 600/509 |
| 5,231,990 A | 8/1993 | Gauglitz |
| 5,271,411 A | 12/1993 | Ripley et al. |
| 5,284,136 A | 2/1994 | Hauck et al. |
| 5,299,118 A * | 3/1994 | Martens et al. ............... 600/509 |
| 5,301,677 A | 4/1994 | Hsung |
| 5,312,445 A | 5/1994 | Nappholz et al. |
| 5,313,953 A | 5/1994 | Yomtov et al. |
| 5,324,310 A | 6/1994 | Greeninger et al. |
| 5,331,966 A | 7/1994 | Bennett et al. |

(Continued)

FOREIGN PATENT DOCUMENTS

| EP | 0560569 | 9/1993 |
| EP | 1038498 | 9/2000 |

(Continued)

OTHER PUBLICATIONS

U.S. Appl. No. 60/844,253, filed Sep. 13, 2006, Johnson et al.
U.S. Appl. No. 11/209,976, filed Aug. 23, 2005, Li et al.
U.S. Appl. No. 11/312,280, filed Dec. 20, 2005, Cazares et al.
U.S. Appl. No. 11/478,286, filed Jun. 29, 2006, Sathaye et al.
U.S. Appl. No. 11/506,253, filed Aug. 18, 2006, Cazares et al.

(Continued)

*Primary Examiner* — Christopher D Koharski
*Assistant Examiner* — Elizabeth K So
(74) *Attorney, Agent, or Firm* — Brooks, Cameron & Huebsch, PLLC

(57) ABSTRACT

Methods and systems for arranging and labeling cardiac episodes based on acquired cardiac episode data are described. Cardiac episodes are algorithmically arranged based on one or more discriminating features of the episode data. A user is presented with at least one episode selected from the arrangement of cardiac episodes. The user inputs a label that characterizes the selected episode. The label is algorithmically appended to the data of the selected episode and to other episodes of the arrangement of cardiac episodes based on the discriminating features.

28 Claims, 11 Drawing Sheets

(56) References Cited

U.S. PATENT DOCUMENTS

| | | | |
|---|---|---|---|
| 5,342,402 A | 8/1994 | Olson et al. |
| 5,350,410 A | 9/1994 | Kleks et al. |
| 5,388,578 A | 2/1995 | Yomtov et al. |
| 5,411,031 A | 5/1995 | Yomtov |
| 5,411,533 A | 5/1995 | Dubreuil |
| 5,431,693 A | 7/1995 | Schroeppel |
| 5,443,485 A | 8/1995 | Housworth et al. |
| 5,545,186 A | 8/1996 | Olson et al. |
| 5,605,158 A * | 2/1997 | Snell .......................... 600/508 |
| 5,620,466 A | 4/1997 | Haefner et al. |
| 5,626,620 A | 5/1997 | Kieval et al. |
| 5,662,688 A | 9/1997 | Haefner et al. |
| 5,674,254 A | 10/1997 | van Krieken |
| 5,683,431 A | 11/1997 | Wang |
| 5,697,959 A * | 12/1997 | Poore .......................... 607/32 |
| 5,704,365 A | 1/1998 | Albrecht et al. |
| 5,735,882 A | 4/1998 | Rottenberg et al. |
| 5,755,737 A | 5/1998 | Prieve et al. |
| 5,779,645 A | 7/1998 | Olson et al. |
| 5,803,084 A | 9/1998 | Olson |
| 5,844,506 A | 12/1998 | Binstead |
| 5,855,593 A | 1/1999 | Olson et al. |
| 5,861,013 A | 1/1999 | Peck et al. |
| 5,871,512 A | 2/1999 | Hemming et al. |
| 5,873,898 A | 2/1999 | Hemming et al. |
| 6,038,474 A | 3/2000 | Zhu et al. |
| 6,044,298 A | 3/2000 | Salo et al. |
| 6,101,416 A | 8/2000 | Sloman |
| 6,115,628 A | 9/2000 | Stadler et al. |
| 6,134,473 A | 10/2000 | Hemming et al. |
| 6,141,581 A | 10/2000 | Olson et al. |
| 6,147,680 A | 11/2000 | Tareev |
| 6,148,230 A | 11/2000 | KenKnight |
| 6,148,234 A | 11/2000 | Struble |
| 6,175,766 B1 | 1/2001 | Bornzin et al. |
| 6,221,011 B1 | 4/2001 | Bardy |
| 6,226,551 B1 | 5/2001 | Zhu et al. |
| 6,253,102 B1 | 6/2001 | Hsu et al. |
| 6,259,947 B1 | 7/2001 | Olson et al. |
| 6,266,554 B1 | 7/2001 | Hsu et al. |
| 6,267,778 B1 | 7/2001 | Cohen |
| 6,280,380 B1 | 8/2001 | Bardy |
| 6,301,503 B1 * | 10/2001 | Hsu et al. .......................... 607/30 |
| 6,324,421 B1 | 11/2001 | Stadler et al. |
| 6,324,427 B1 | 11/2001 | Florio |
| 6,345,201 B1 | 2/2002 | Sloman et al. |
| 6,368,284 B1 | 4/2002 | Bardy |
| 6,393,316 B1 | 5/2002 | Gillberg et al. |
| 6,409,675 B1 | 6/2002 | Turcott |
| 6,418,340 B1 | 7/2002 | Conley et al. |
| 6,434,428 B1 | 8/2002 | Sloman et al. |
| 6,438,409 B1 * | 8/2002 | Malik et al. .................... 600/512 |
| 6,438,410 B2 | 8/2002 | Hsu et al. |
| 6,440,066 B1 | 8/2002 | Bardy |
| 6,449,503 B1 | 9/2002 | Hsu |
| 6,456,880 B1 | 9/2002 | Park et al. |
| 6,456,881 B1 | 9/2002 | Bornzin et al. |
| 6,477,422 B1 | 11/2002 | Splett |
| 6,480,733 B1 | 11/2002 | Turcott |
| 6,487,443 B2 | 11/2002 | Olson et al. |
| 6,491,639 B1 | 12/2002 | Turcott |
| 6,496,715 B1 | 12/2002 | Lee et al. |
| 6,505,067 B1 | 1/2003 | Lee et al. |
| 6,512,940 B1 | 1/2003 | Brabec et al. |
| 6,512,953 B2 | 1/2003 | Florio et al. |
| 6,522,915 B1 | 2/2003 | Ceballos et al. |
| 6,564,106 B2 | 5/2003 | Guck et al. |
| 6,597,951 B2 | 7/2003 | Kramer et al. |
| 6,618,619 B1 | 9/2003 | Florio et al. |
| 6,622,046 B2 | 9/2003 | Fraley et al. |
| 6,625,490 B1 | 9/2003 | McClure et al. |
| 6,631,290 B1 | 10/2003 | Guck et al. |
| 6,654,637 B2 | 11/2003 | Rouw et al. |
| 6,690,967 B2 | 2/2004 | Meij |
| 6,708,058 B2 | 3/2004 | Kim et al. |
| 6,725,085 B2 | 4/2004 | Schwartzmann et al. |
| 6,738,669 B1 | 5/2004 | Sloman et al. |
| 6,754,523 B2 | 6/2004 | Toole |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,768,923 B2 | 7/2004 | Ding et al. |
| 6,768,924 B2 | 7/2004 | Ding et al. |
| 6,856,835 B2 | 2/2005 | Bardy et al. |
| 6,881,192 B1 | 4/2005 | Park |
| 6,885,893 B1 | 4/2005 | Lu |
| 6,888,538 B2 | 5/2005 | Ely et al. |
| 6,889,079 B2 | 5/2005 | Bocek et al. |
| 6,904,315 B2 | 6/2005 | Panken et al. |
| 6,925,330 B2 | 8/2005 | Kleine |
| 6,944,495 B2 | 9/2005 | MacAdam et al. |
| 6,950,702 B2 | 9/2005 | Sweeney |
| 6,952,610 B2 | 10/2005 | Ostroff |
| 6,959,214 B2 | 10/2005 | Pape et al. |
| 6,961,613 B2 | 11/2005 | Bjorling et al. |
| 6,973,350 B1 | 12/2005 | Levine et al. |
| 6,975,904 B1 | 12/2005 | Sloman |
| 6,988,003 B2 | 1/2006 | Bardy et al. |
| 6,993,379 B1 | 1/2006 | Kroll |
| 6,999,817 B2 | 2/2006 | Park et al. |
| 7,006,869 B2 | 2/2006 | Bradley |
| 7,027,861 B2 | 4/2006 | Thompson |
| 7,039,459 B2 | 5/2006 | Bardy |
| 7,043,299 B2 | 5/2006 | Erlinger |
| 7,065,400 B2 | 6/2006 | Schechter |
| 7,065,410 B2 | 6/2006 | Bardy et al. |
| 7,085,599 B2 | 8/2006 | Kim et al. |
| 7,090,682 B2 | 8/2006 | Sanders et al. |
| 7,092,754 B2 | 8/2006 | Bardy et al. |
| 7,103,404 B2 | 9/2006 | Staler et al. |
| 7,113,823 B2 | 9/2006 | Yonce et al. |
| 7,117,036 B2 | 10/2006 | Florio |
| 7,120,495 B2 | 10/2006 | Bardy et al. |
| 7,127,290 B2 | 10/2006 | Girouard |
| 7,139,610 B2 | 11/2006 | Ferek-Patric |
| 7,146,206 B2 | 12/2006 | Glass et al. |
| 7,177,689 B2 | 2/2007 | Ternes et al. |
| 7,191,003 B2 | 3/2007 | Greenhut et al. |
| 7,191,004 B2 | 3/2007 | Kim et al. |
| 7,194,309 B2 | 3/2007 | Ostroff et al. |
| 7,203,542 B2 | 4/2007 | Obel |
| 7,203,543 B2 | 4/2007 | Meyer et al. |
| 7,212,862 B2 | 5/2007 | Park et al. |
| 7,225,021 B1 | 5/2007 | Park et al. |
| 7,228,173 B2 | 6/2007 | Cazares |
| 7,236,819 B2 | 6/2007 | Brockway |
| 7,242,978 B2 * | 7/2007 | Cao et al. ...................... 600/518 |
| 7,245,962 B2 | 7/2007 | Ciaccio et al. |
| 7,263,399 B2 | 8/2007 | Carlson |
| 7,277,754 B2 | 10/2007 | McCabe et al. |
| 7,286,876 B2 | 10/2007 | Yonce et al. |
| 7,299,086 B2 | 11/2007 | McCabe et al. |
| 7,319,900 B2 | 1/2008 | Kim et al. |
| 7,457,664 B2 | 11/2008 | Zhang et al. |
| 7,477,932 B2 | 1/2009 | Lee |
| 7,558,628 B2 | 7/2009 | Yonce et al. |
| 7,818,056 B2 * | 10/2010 | Kim et al. ...................... 607/5 |
| 2002/0082658 A1 | 6/2002 | Heinrich et al. |
| 2002/0095184 A1 | 7/2002 | Bardy et al. |
| 2002/0107544 A1 | 8/2002 | Ostroff et al. |
| 2002/0120311 A1 | 8/2002 | Lindh et al. |
| 2003/0212436 A1 | 11/2003 | Brown |
| 2004/0064159 A1 | 4/2004 | Hoijer et al. |
| 2004/0172065 A1 | 9/2004 | Sih et al. |
| 2004/0215240 A1 | 10/2004 | Lovett et al. |
| 2004/0215277 A1 | 10/2004 | Oosterhoff et al. |
| 2004/0230128 A1 | 11/2004 | Brockway et al. |
| 2004/0239650 A1 | 12/2004 | Mackey |
| 2004/0243014 A1 | 12/2004 | Lee et al. |
| 2004/0260351 A1 | 12/2004 | Holmstrom et al. |
| 2005/0004486 A1 | 1/2005 | Glass et al. |
| 2005/0004612 A1 | 1/2005 | Scholten et al. |
| 2005/0038478 A1 | 2/2005 | Klepfer et al. |
| 2005/0131477 A1 | 6/2005 | Meyer et al. |

(56) References Cited

U.S. PATENT DOCUMENTS

| | | |
|---|---|---|
| 2005/0131478 A1 | 6/2005 | Kim et al. |
| 2005/0137485 A1 | 6/2005 | Cao et al. |
| 2005/0288600 A1 | 12/2005 | Zhang et al. |
| 2006/0047319 A1 | 3/2006 | Bruhns et al. |
| 2006/0069322 A1 | 3/2006 | Zhang et al. |
| 2006/0074331 A1 | 4/2006 | Kim et al. |
| 2006/0111747 A1 | 5/2006 | Cazares et al. |
| 2006/0111751 A1 | 5/2006 | Cazares |
| 2006/0116593 A1 | 6/2006 | Zhang et al. |
| 2006/0129194 A1 | 6/2006 | Zhang |
| 2006/0129196 A1 | 6/2006 | Dong et al. |
| 2006/0247695 A1 | 11/2006 | Stalsberg et al. |
| 2006/0253043 A1 | 11/2006 | Zhang et al. |
| 2006/0253044 A1 | 11/2006 | Zhang et al. |
| 2006/0253164 A1 | 11/2006 | Zhang et al. |
| 2008/0004665 A1 | 1/2008 | McCabe et al. |
| 2009/0312813 A1 | 12/2009 | Cazares |

FOREIGN PATENT DOCUMENTS

| | | |
|---|---|---|
| EP | 1291038 | 3/2003 |
| WO | WO9217240 | 10/1992 |
| WO | WO9220402 | 11/1992 |
| WO | WO0240097 | 5/2002 |
| WO | WO0247761 | 6/2002 |
| WO | WO02087696 | 11/2002 |
| WO | WO03003905 | 1/2003 |
| WO | WO03028550 | 4/2003 |
| WO | WO2004026398 | 4/2004 |
| WO | WO2005058412 | 6/2005 |
| WO | WO2005089865 | 9/2005 |
| WO | WO2006065707 | 6/2006 |
| WO | WO2008005270 | 1/2008 |

OTHER PUBLICATIONS

Schuder et al., "*Transthoracic Ventricular Defibrillation in the Dog with Truncated and Untruncated Exponential Stimuli*", IEEE Transitions on Bio-Medical Engineering, vol. BME-18, No. 6, pp. 410-415, (Nov. 1971).

Smits et al., "*Defibrillation Threshold (DFT) Model of a Fully Subcutaneous ICD System*", Europace Supplements, vol. 2, at col. 778, p. B83, (Jun. 2001).

Splett et al. "Determination of Pacing Capture in Implantable Defibrillators: Benefit of Evoked Response Detection Using RV Coil to Can Vector," *PACE*, vol. 23, pp. 1645-1650, (2000).

Acar et al., "*SVD-based on-line exercise ECG signal orthogonalization*", IEEE Transactions on Biomedical Engineering, vol. 46, No. 3, (Mar. 1999). Abstract only.

A. Hyvärinen and E. Oja, *Independent Component Analysis: A Tutorial*, Helsinki Univ. of Technology, (Apr. 1999).

Adel Belouchrani and Moeness G. Amin, *Blind Source Separation Based on Time-Frequency Signal Representations*, IEEE Transactions on Signal Processing, vol. 46, No. 11, pp. 2888-2897 (Nov. 1998).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

J.J. Rieta, et al., *Atrial Activity Extraction Based on Blind Source Separation as an Alternative to QRST Cancellation for Atrial Fibrillation Analysis*, Computers in Cardiology, vol. 27, pp. 69-72 (2000).

John C. Schuder et al., *Experimental Ventricular Defibrillation with an Automatic and Completely Implanted System*, Trans. Am. Soc. Artif. Int. Organs, vol. 16, pp. 207-212 (1970).

John C. Schuder et al., *Ventricular Defibrillation in the Dog Using Implanted and Partially Implanted Electrode Systems*, Am. J. of Cardiology, vol. 33, pp. 243-247 (Feb. 1974).

Krahn, A.D. et al. *Recurrent syncope. Experience with an implantable loop record*. Cardiol. Clin., vol. 15(2), (May 1997), pp. 316-326.

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Philippe Gallois, et al., *Multi-Channel Analysis of the EEG Signals and Statistic Particularities for Epileptic Seizure Forecast*, Second Joint EMBS/BMES Conference, pp. 208-215 (Oct. 23-26, 2002).

Pierre Comon, *Independent component analysis, A new concept?*, Signal Processing, vol. 36, No. 3, pp. 287-314, (Apr. 1994).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

Theofilos M. Kolettis, MD, PhD et al., *Submammary Implantation of a Cardioverter-Defibrillator with a Nonthoractomy Lead System*, Am. Heart J., vol. 126, pp. 1222-1223 (Nov. 1993).

Vicente Zarzoso and Asoke K. Nandi, *Blind Separation of Independent Sources for Virtually Any Source Probability Density Function*, IEEE Transactions on Signal Processing, vol. 47, No. 9, pp. 2419-2432 (Sep. 1999).

Vicente Zarzoso and Asoke K. Nandi, *Noninvasive Fetal Electrocardiogram Extraction: Blind Separation Versus Adaptive Noise Cancellation*, IEEE Transactions on Biomedical Engineering, vol. 48, No. 1, pp. 12-18 (Jan. 2001).

Wilkoff BL, et al., *Preventing Shocks after ICD Implantation: Can a Strategy of Standardized ICD Programming Match Physician Tailored*? Late Breaking Trials, HRS (2005).

Cohen et al. Capture Management Efficacy in children and young adults with endocardial and unipolar epicardial systems. Europace, vol. 6, pp. 248-255 (2004).

Office Action dated May 18, 2010 from U.S. Appl. No. 11/478,286, 13 pages.

Office Action Response dated Mar. 11, 2010 from U.S. Appl. No. 11/478,286, 12 pages.

Office Action dated Dec. 23, 2009 from U.S. Appl. No. 11/478,286, 12 pages.

Office Action Response dated Oct. 7, 2009 from U.S. Appl. No. 11/478,286, 9 pages.

Office Action dated Aug. 7, 2009 from U.S. Appl. No. 11/478,286, 3 pages.

Office Action Response dated Jul. 27, 2009 from U.S. Appl. No. 11/478,286, 12 pages.

Office Action dated Jun. 8, 2009 from U.S. Appl. No. 11/478,286, 10 pages.

Office Action Response dated Feb. 27, 2009 from U.S. Appl. No. 11/478,286, 12 pages.

Notice of Allowance dated May 1, 2009 from U.S. Appl. No. 11/506,253, 9 pages.

Office Action Response dated Feb. 24, 2009 from U.S. Appl. No. 11/506,253, 8 pages.

Office Action dated Nov. 7, 2008 from U.S. Appl. No. 11/506,253, 9 pages.

Interview Summary dated Jan. 30, 2009 from U.S. Appl. No. 11/478,286, 4 pages.

Office Action dated Oct. 29, 2008 from U.S. Appl. No. 11/478,286, 13 pages.

International Preliminary Report on Patentability dated Jan. 15, 2009 from PCT Application No. PCT/US2007/014968, 10 pages.

International Search Report and Written Opinion dated Feb. 19, 2008 from PCT Application No. PCT/US2007/014968, 15 pages.

Office Action dated Aug. 2, 2010 from U.S. Appl. No. 11/478,286, 14 pages.

Interview Summary dated Sep. 20, 2010 from U.S. Appl. No. 11/478,286, 3 pages.

Office Action Response dated Oct. 5, 2010 from U.S. Appl. No. 11/478,286, 12 pages.

Stirbis et al., Optimizing the Shape of Implanted Artificial Pacemakers, Kaunas Medical Institute. Translated from Meditsinskaya Tekhnika, No. 6, pp. 25-27, 1986.

File History for U.S. Appl. No. 12/545,364.

* cited by examiner

SYSTEMS AND METHODS FOR ARRANGING AND LABELING CARDIAC EPISODES

RELATED APPLICATIONS

This application claims the benefit of Provisional Patent Application Ser. No. 60/844,482, filed on Sep. 14, 2006, to which priority is claimed pursuant to 35 U.S.C. §119(e) and which is hereby incorporated herein by reference.

FIELD OF THE INVENTION

The present invention relates generally to cardiac devices and methods, and, more particularly, to arranging and labeling various types of cardiac episodes based on one or more discriminating features of the episodes.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in an atrial region of the heart is denoted a supra-ventricular tachyarrhythmia (SVT). Atrial fibrillation and atrial flutter are examples of SVT. Both conditions are characterized by rapid, uncoordinated contractions of the atria resulting in hemodynamically inefficient pumping action.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria resulting in hemodynamically efficient pumping action, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmias. Ventricular tachycardia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable medical devices, including pacemakers and implantable cardioverter/defibrillators (ICDs), and have been used to deliver effective treatment to patients with serious cardiac arrhythmias. Implantable medical devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the ICD must first identify the type of arrhythmia that is occurring, after which appropriate therapy may be delivered to the heart.

In addition to arrhythmic episodes, patients may experience other types of cardiac episodes. Various types of cardiac episodes may be detected by analysis of various sensor signals available to the ICD, such as cardiac electrical signals sensed by the ICD electrodes, hemodynamic sensor signals, activity signals, posture signals, respiration signals, and/or signals produced by other types of sensors. For example, patients suffering from congestive heart failure may experience periods of cardiac decompensation when the heart fails to adequately pump blood to the tissues of the body. In another example, patients may experience myocardial ischemia when there is insufficient blood supply to the heart. If the blood supply is severely interrupted, myocardial infarction may occur. These episodes are detectable by characteristic sensor signals present before, during, and/or after the episode occurs. Methods and systems that facilitate identification of these and other cardiac episodes aid in delivering appropriate therapy to treat the disorders causing the episodes.

SUMMARY OF THE INVENTION

The present invention is directed to methods and systems for arranging and labeling cardiac episodes. One embodiment is directed to a method operable on cardiac episode data acquired by an implantable cardiac device. The cardiac episodes are algorithmically arranged based on one or more discriminating features of the episodes. A user is presented with at least one episode selected from the arrangement of cardiac episodes. The user inputs a label that characterizes the selected episode. The label is algorithmically appended to the data of the selected episode and to other episodes of the arrangement of cardiac episodes based on the episodes' discriminating features. In one implementation, the cardiac episodes are arranged based on the similarity of the one or more discriminating features.

The episodes may be arranged by ordering the episodes, grouping the episodes, grouping the episodes after they are ordered, or ordering the episodes after they are grouped. The number of groups used for the grouping may be determined by a user or may be determined algorithmically. According to various examples of arranging the ordered episodes, the ordered episodes may be grouped based on one or more boundary episodes identified by the user or algorithmically identified. If the group or boundary episodes are algorithmically determined, the user may have the opportunity to override these algorithmic determinations and substitute groupings or boundary episodes identified by the user.

The data used to identify the episodes may include cardiac electrical signals such as electrogram (EGM) signals and/or electrocardiogram (ECG) signals acquired before, during and/or after the episodes via implantable or non-implantable cardiac electrodes. After arranging and labeling the episodes, data from additional episodes may be acquired. The process of arranging and labeling the data may be repeated using the additional episode data. Repeating the algorithmic arranging and appending processes may be initiated algorithmically or manually.

According to one aspect of the invention, presenting the at least one episode to the user involves graphically displaying a cardiac signal associated with the cardiac episode.

The one or more discriminating features of the episodes may characterize a conduction pattern of an arrhythmic episode or a type of arrhythmia. In one implementation, the label characterizes at least some of the cardiac episodes as tachyarrhythmia episodes that are ventricular in origin or supraventricular in origin. In another implementation, the label characterizes at least some of the cardiac episodes as tachyarrhythmia episodes that are hemodynamically stable or hemodynamically unstable. In yet another implementation, the label characterizes at least some of the arrhythmia episodes as tachyarrhythmia episodes that should be treated with anti-tachyarrhythmia therapy or those that should not be treated with anti-tachyarrhythmia therapy. The anti-tachyarrhythmia therapy may include defibrillation, cardioversion, and/or anti-tachyarrhythmia pacing.

In one configuration, at least one of algorithmically arranging, receiving the user-selected label, and algorithmically appending the label is implementable by the implantable cardiac device. In another configuration, at least one of algorithmically arranging, presenting the at least one episode to the user, receiving the user-selected label, and algorithmically appending is implemented by a processor external of the implantable cardiac device.

Another embodiment of the invention is directed to a cardiac system configured to arrange and label episode data. The system includes sensing circuitry configured to acquire data associated with cardiac episodes. A user interface presents data of a selected cardiac episode to a user and to receive a user-selected label for the episode. A data processor arranges the cardiac episode data based on one or more discriminating features of the episodes and appends the label to the data of the selected cardiac episode and to data of other cardiac episodes having features that are similar to the discriminating features.

The sensing system includes cardiac electrodes configured to sense local and/or non-local cardiac electrical signals. The system may include additional sensors configured to acquire additional data related to the cardiac episodes that are used for arranging and labeling the episodes. The additional sensors may acquire physiological and/or non-physiological data associated with the cardiac episodes other than the cardiac electrical signals. The additional sensors may include, for example, hemodynamic sensors, pressure sensors, chemical sensors, activity sensors, posture sensors, respiration sensors, and/or any other types of sensors that are capable of acquiring data relating to cardiac episodes.

According to one implementation, at least one of the sensing circuitry and data processor are components of an implantable cardiac device. In another implementation, the sensing circuitry is a component of an implantable device and the user interface and data processor are components of a non-implantable device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
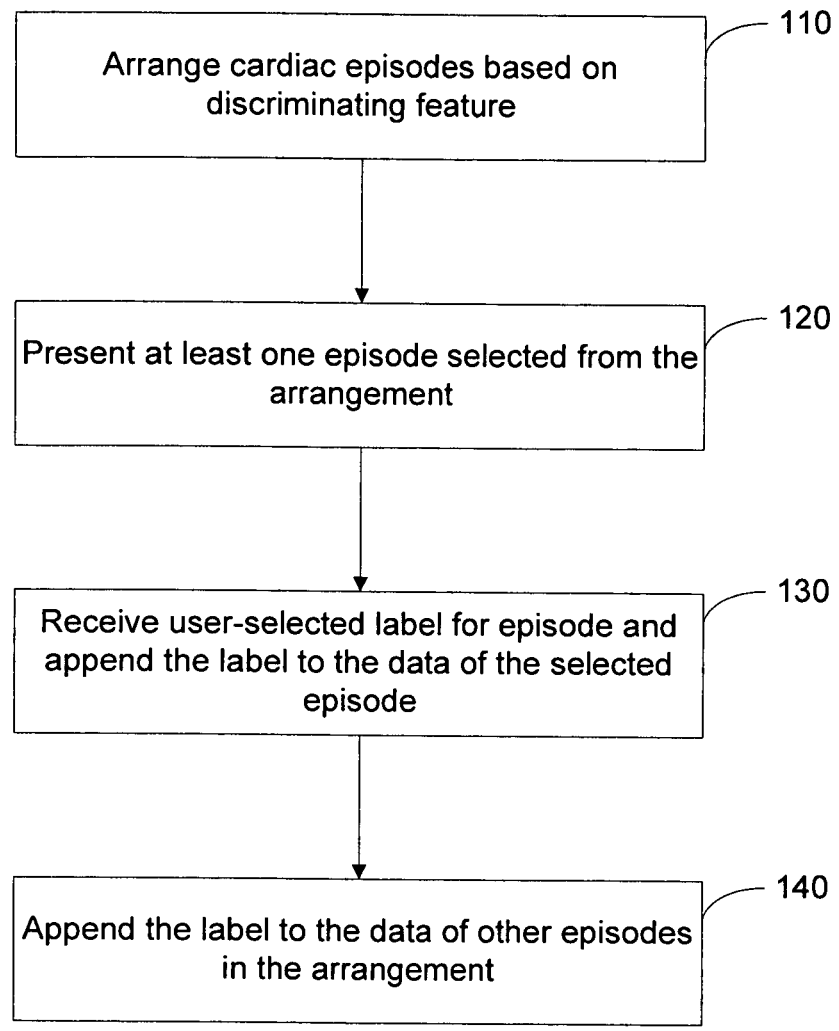
FIGS. 1A and 1B are flowcharts illustrating methods for arranging and labeling cardiac episodes based on data collected by an implantable or non-implantable device in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternative falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The present invention is directed to methods and systems for arranging and labeling cardiac episodes based on discriminating features of cardiac episode data. In various implementations, an implantable or non-implantable cardiac device may acquire data related to various types of cardiac episodes by sensing cardiac electrical signals, and optionally other physiological or non-physiological signals, before, during, and/or after the occurrence of the episodes. One or more discriminating features of the cardiac episodes are extracted from the acquired data. For example, one or more discriminating features of the cardiac electrical signals of an episode may characterize the type of conduction pattern of an episode. The cardiac episodes are arranged and labeled based on the discriminating features.

Embodiments of the invention presented herein are described in conjunction with arranging and labeling cardiac tachyarrhythmia episodes, although the principles of the invention are equally applicable for arranging and labeling cardiac episodes of any type. In various implementations, cardiac episodes other than or in addition to tachyarrhythmia episodes may be arranged and labeled, such as cardiac decompensation episodes, ischemic episodes, myocardial infarction episodes, and/or other types of cardiac episodes. The examples presented herein provide processes for quickly identifying cardiac episodes that occur most frequently or that have significant impact to the patient. Identification and labeling of frequently occurring episode types provides useful diagnostic information, allows for verification of therapy effectiveness, and facilitates formation of templates for subsequent identification of similar episodes.

A tachyarrhythmia episode typically includes a number of fast cardiac beats. Arrhythmias that originate in the ventricles, such as ventricular tachyarrhythmia (VT) or ventricular fibrillation (VF) can be discriminated from normal sinus rhythm (NSR) or supraventricular tachyarrhythmias (SVT) that originate in the atria from EGM and/or ECG signals. Discrimination between types of VT and/or between VT/VF and SVT may be achieved based on analysis of various features of the cardiac signals of the tachyarrhythmia episode beats. For example, discrimination between these different types of arrhythmias may be accomplished by analyzing the heart rate of the atrial and/or ventricular chambers, the onset conditions of the arrhythmic episode, the stability of the atrial and/or ventricular rhythms during the episode, the duration of the episode, and/or other features of the episode. The morphology of individual cardiac beat signals of the arrhythmic episode may be analyzed to classify the arrhythmia as a particular type of VT and/or to discriminate between VT/VF and SVT.

Implantable cardioverter/defibrillators (ICDs) include electrodes implanted in, on or about the heart or subcutaneously under the surface of the patient's skin which are used to sense cardiac electrical signals and/or to deliver electrical stimulation therapy. ICDs may have the capability to provide tiered therapy options for treating different types of arrhythmias. For example, if an arrhythmia episode is identified as SVT, the ICD may withhold therapy, if an arrhythmia episode is identified as VT or VF, the ICD may deliver anti-tachyarrhythmia pacing or defibrillation shocks.

An ICD in accordance with embodiments of the invention has the capability to acquire data related to the cardiac episodes, including cardiac electrical signals sensed by the device before, during and/or after the episode. The acquired data may be analyzed to diagnose various disorders, verify the efficacy of arrhythmia detection, verify the adequacy of therapy delivery and/or improve the programmable device settings, among other things. The cardiac electrical signals acquired by the ICD may include collect locally sensed and/or non-locally sensed cardiac signals.

Local sensing using an electrode in contact with or in close proximity to the myocardial tissue yields signals that are most strongly representative of the activation signals that are present close to the site of the electrode. Local signals may be sensed using cardiac electrodes inserted into the heart or cardiac vasculature or arranged on the outside of the heart, for example.

Non-local sensing of the cardiac signals may be achieved via electrodes that are electrically coupled to, but do not make direct contact with the myocardium. A sensed non-local cardiac beat signal is effectively a superposition of a number of activation signals occurring within the heart that are associated with a cardiac contraction. In one approach, non-local sensing vectors may include a number of subcutaneous electrodes disposed on the housing or header of a cardiac pacemaker or defibrillator. Various aspects of local and non-local cardiac sensing are described in commonly owned U.S. Patent Publication No. 2008/0009909 which is incorporated herein by reference. The local or non-local cardiac signals are acquired by the device and may be stored in the device, optionally along with additional data acquired from physiological or non-physiological sensors. The additional data may include information such as time and day of the episode, episode duration, therapy delivered, therapy success, and/or other data.

As previously discussed, an ICD may be used to acquire episode data. For patients without an ICD, a non-implantable device, such as a patient worn or carried cardiac monitor may be used to acquire cardiac signals and/or data from additional sensors before, during, or after cardiac episodes. In non-implantable configurations, the cardiac signals are sensed using electrodes attached or arranged on the surface of the patient's body.

In some configurations, the implantable or non-implantable device used to acquire the data may interface with a separate device such as a device programmer or advanced patient management (APM) server to facilitate user interaction with the episode data. For example, stored episode data may be downloaded from an ICD or patient-external cardiac monitor to the device programmer having a user interface to facilitate input and output operations. For example, a physician may review episode data viewable on display screen or other output device and may input labels for the episodes through a keyboard, mouse or other input device.

In one example, the physician may observe the graphical representation of the cardiac beat signals recorded by an ICD during a tachyarrhythmia episode and classify the episode as a VT episode or SVT episode. After the physician classifies the arrhythmia episode as SVT or VT, an SVT or VT template may be formed representing a one beat of the SVT or VT episode. The template may be uploaded to the ICD and subsequently used by the ICD to identify subsequent similar episodes.

The flowchart of FIG. 1A illustrates a method for arranging and labeling cardiac episode based on episode data collected by an implantable or non-implantable device in accordance with embodiments of the invention. Such a process may be implemented, for example, via an ICD device programmer or other device that includes an interface for interacting with a user. The method involves algorithmically arranging 110 cardiac episodes based on one or more discriminating features of the episode data. At least one episode selected from the arrangement of episodes is presented 120 to a user. The user chooses a label that characterizes the selected episode. The label is received 130 by the device and is algorithmically appended 140 to the data of selected episode and the data of other episodes of the arrangement of cardiac episodes. For example, the device may identify other episodes having features similar to the selected and labeled episode and append the label to the data of similar episodes.

In some implementations, a label may be algorithmically selected by the device, e.g., VT1, VT2, SVT1, SVT2, or other label. In this situation, the physician may be provided the opportunity to override the algorithmically selected label and select a different label, or may confirm the label provided by the device.

Figure 1B:
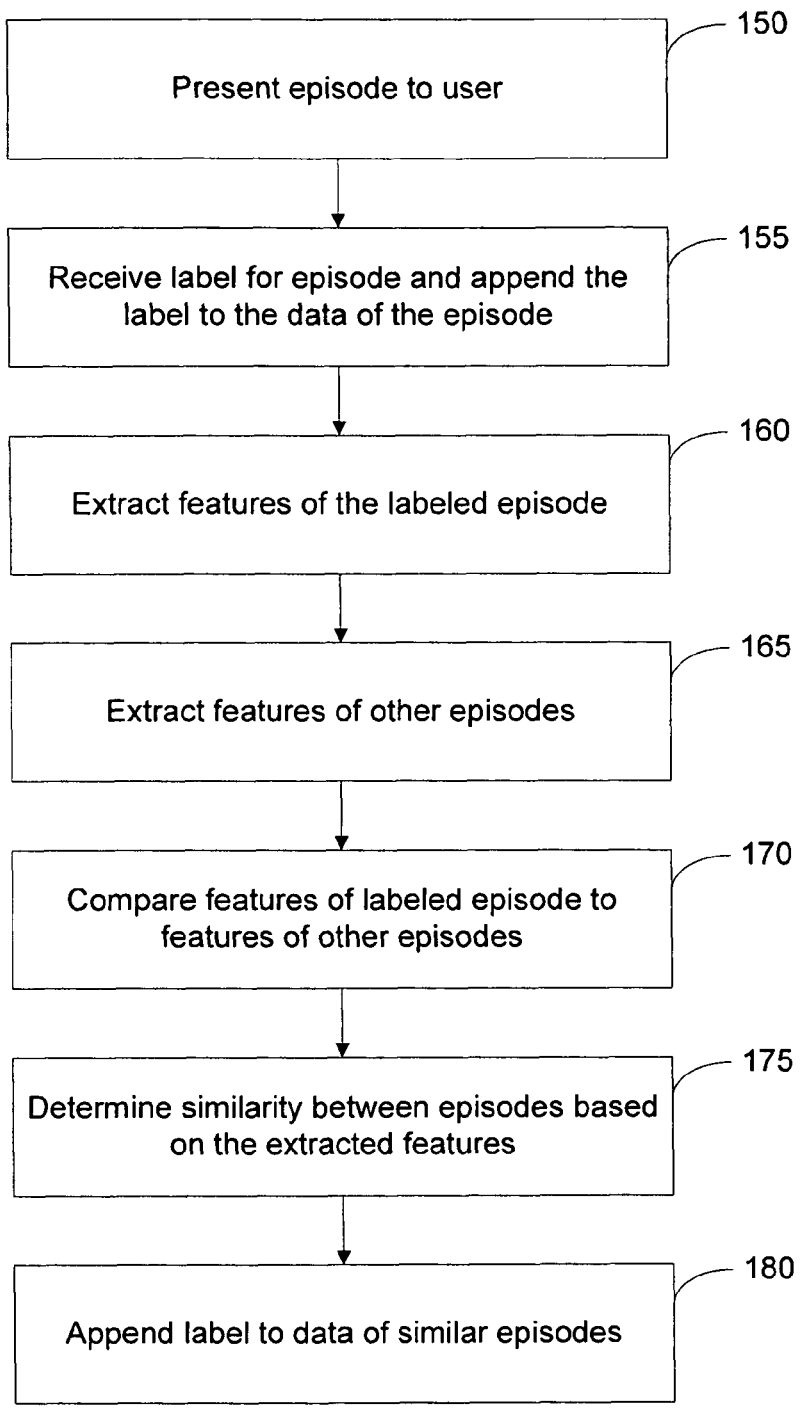

The flowchart of FIG. 1B illustrates a method for arranging and labeling episode data in accordance with another embodiment. An episode is presented 150 to a user, such as via a graphical display on a device programmer. The user selects a label for the episode presented on the display and enters 155 a label for the episode into the device programmer. Discriminating features of the selected episode are extracted 160 from the episode data of the selected episode. Features of other stored episodes are extracted 165 and are compared 170 to the features of the labeled episode. The similarity between the episodes and the labeled episode is determined 175. The label entered by the user is appended 180 to the data of the similar episodes.

Figure 2:
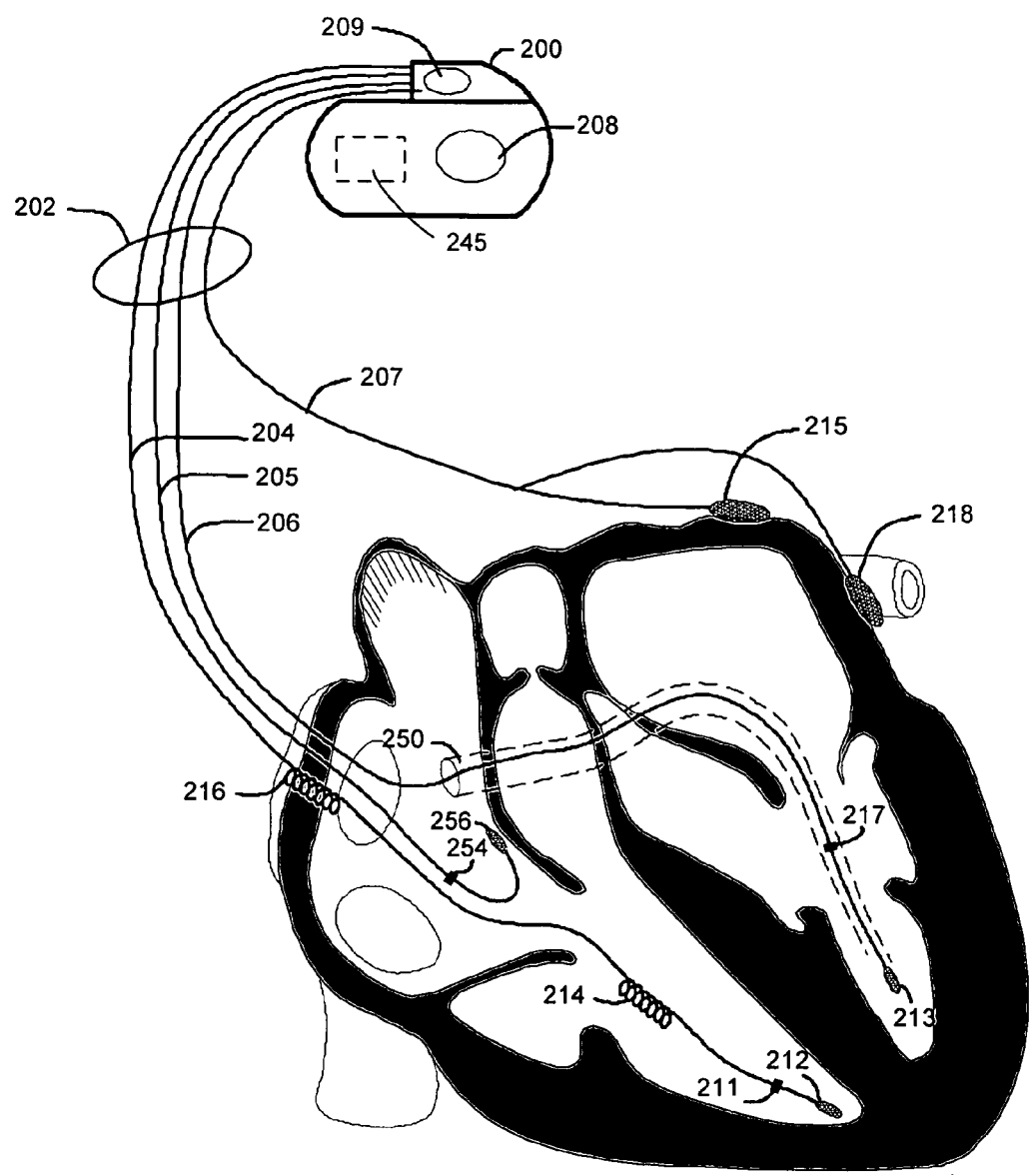
FIG. 2 shows an implantable cardiac device configured to acquire data related to cardiac episodes that may be arranged and labeled in accordance with embodiments of the invention.

Referring now to FIG. 2 of the drawings, there is shown an ICD configured to acquire cardiac episode data for subsequent arrangement and labeling of cardiac episodes in accordance with principles of the present invention. The ICD 200 in FIG. 2 may include pacemaker and/or defibrillator circuitry enclosed within a housing and coupled to a lead system 202. The housing and/or header of the device 200 may incorporate one or more can or indifferent electrodes 208, 209 used to provide electrical stimulation energy to the heart and/or to sense cardiac electrical activity. The ICD 200 may utilize all or a portion of the device housing as a can electrode 208 and/or may have multiple can electrically isolated electrodes disposed on the housing. The ICD 200 may include one or more indifferent electrodes 209 positioned, for example, on the header or the housing of the ICD 200.

The lead system 202 is used to sense cardiac electrical signals produced by the heart and to provide electrical energy to the heart under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, and an intracardiac left ventricular (LV) lead system 206. An extracardiac left atrial (LA) lead system 207 may optionally be employed.

The ICD 200 and lead system 202 illustrated in FIG. 2 are configured for biventricular or biatrial sensing and/or pacing. The lead system 202 of FIG. 2 illustrates one embodiment that may be used in connection with the processes described herein. Other leads and/or electrodes may additionally or alternatively be used. For example, the lead system 202 may include multiple electrodes in one chamber configured for intrachamber pacing and sensing. In this configuration, the ICD 200 may pace and/or sense at multiple sites in one cardiac chamber via multiple electrodes within the chamber. This type of multisite pacing and sensing may be employed in one or more of the right atrium, left atrium, right ventricle or left ventricle. Multisite pacing in a chamber may be used for example, to increase the power and/or synchrony of cardiac contractions of the paced chamber.

As illustrated in FIG. 2, the lead system 202 may include one or more extracardiac leads 207 having electrodes 215, 218, e.g., epicardial electrodes, patch electrodes or other types of extracardiac electrodes positioned at locations outside the heart for sensing and pacing one or more heart chambers. In various configurations, the epicardial electrodes may be placed on or about the outside of the heart and/or may be embedded in the myocardium from the locations outside the heart.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium and into the right ventricle. In particular, the RV-tip electrode 212, RV-ring electrode 211, and RV-coil electrode 214 are positioned at appropriate locations within the right ventricle for sensing right ventricular cardiac signals and delivering electrical stimulation pulses to the heart. The SVC-coil 216 is positioned at an appropriate location within the right atrium chamber of the heart or a major vein leading to the right atrial chamber.

In one configuration, the RV-tip electrode 212 referenced to the can electrode 208 may be used to implement unipolar pacing and/or sensing in the right ventricle. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle for pacing and/or sensing the left ventricle. The left ventricular lead 206 may be guided into the right atrium of the heart via the superior vena cava. From the right atrium, the left ventricular lead 206 may be deployed into the coronary sinus ostium, the opening of the coronary sinus 250. The lead 206 may be guided through the coronary sinus 250 to a coronary vein of the left ventricle. This vein is used as an access pathway for leads to reach the surfaces of the left ventricle which are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or sensing in the left ventricle may be implemented, for example, using the LV distal electrode 213 referenced to the can electrode 208. The LV distal electrode 213 and the LV proximal electrode 217 may be used together as bipolar sense and/or pace electrodes for the left ventricle. The lead system 202 in conjunction with the device 200 may provide bradycardia pacing therapy to maintain a hemodynamically sufficient heart rate. The left ventricular lead 206 and the right ventricular lead 204 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 205 includes a RA-tip electrode 256 and an RA-ring electrode 254 positioned at appropriate locations in the right atrium for sensing and pacing the right atrium. In one configuration, the RA-tip 256 referenced to the can electrode 208, for example, may be used to provide unipolar pacing and/or sensing in the right atrium. In another configuration, the RA-tip electrode 256 and the RA-ring electrode 254 may be used to effect bipolar pacing and/or sensing.

As previously described, the housing of the ICD 200 may include multiple can electrodes disposed on the housing. Pairs of the can electrodes may be used in non-local sensing of cardiac signals.

The ICD 200 can be programmed to acquire the cardiac signals sensed via electrodes 211-218, 254, 256, 208 and 209 during cardiac episodes such as tachyarrhythmia episodes and/or other types of cardiac episodes. In one implementation, the device circuitry includes a memory 245 for storing cardiac signals and/or other data related to the episodes. The ICD 200 also includes communication circuitry (not shown) to facilitate wireless communication with a patient-external device, such as a device programmer. The cardiac signals and/or other data may be acquired and stored in the ICD memory 245. The signals and data stored in the memory 245 may downloaded to a remote system via the communications circuitry for further analysis.

Although the ICD 200 is described as an implantable device, the device that acquires the episode data need not be implantable and need not have therapy capability. For example, the principles of the invention are also applicable using a cardiac monitor that is patient-external and only acquires and optionally stores cardiac signals and/or other data and without delivering therapy.

Figure 3:
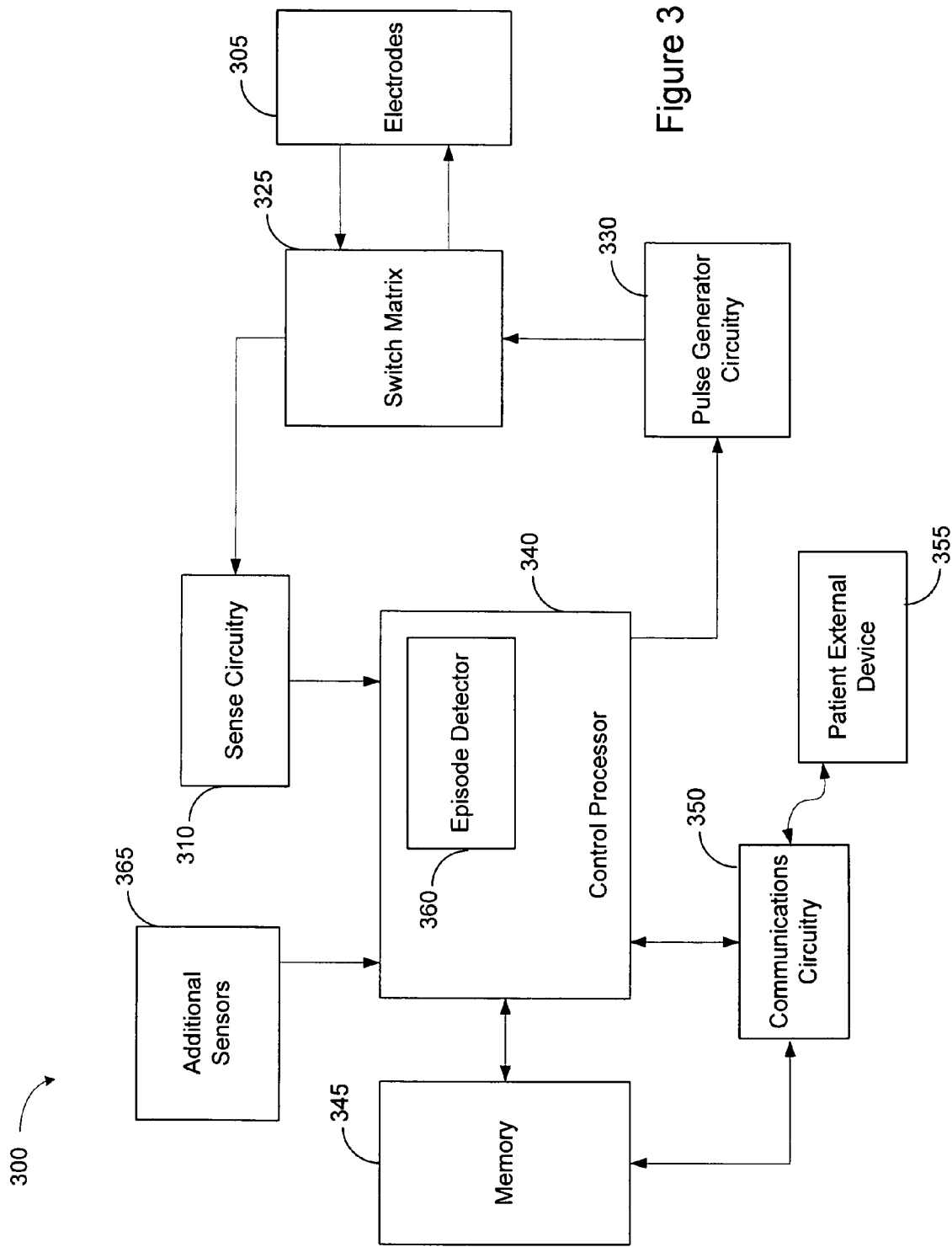
FIG. 3 depicts a block diagram of a system suitable for acquiring cardiac episode data and for arranging and labeling cardiac episodes in accordance with embodiments of the present invention.

Referring now to FIG. 3, there is shown a block diagram of an embodiment of a system 300 suitable for acquiring episode data and arranging and labeling cardiac episodes in accordance with embodiments of the present invention. FIG. 3 shows a system 300 divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used. In addition, although the system 300 depicted in FIG. 3 contemplates the use of programmable microprocessor-based logic circuits, other circuit implementations may be utilized.

The system 300 includes a control processor 340 optionally having an episode detector 360 for detecting tachyarrhythmia episodes and/or other types of cardiac episodes. The episode detector 360 may include circuitry for triggering data acquisition before, during and/or after the occurrence of a cardiac episode. The types of cardiac episodes for which data is acquired may be a programmable option, for example. Collection (i.e., acquisition and storage) of cardiac signal data and optionally other data only during time windows around episode occurrences may be useful in devices where memory is limited. Alternatively, if the system includes sufficient memory, cardiac signals may be continuously collected for later analysis to detect episode occurrences. Alternatively, the device may continuously or intermittently transmit the data in real time as it is acquired to a remote device.

The system 300 may optionally have therapy capability. In therapy-capable implementations, the control processor 340 controls therapy circuitry which is exemplified in the illustrated embodiment by pulse generator circuitry 330. The pulse generator circuitry 330 has the ability to generate pacing pulses for treating bradyarrhythmia and/or the ability to generate anti-tachyarrhythmia pacing pulses and/or high energy defibrillation or cardioversion shocks used for terminating dangerous tachyarrhythmias.

The system 300 senses cardiac signals via multiple cardiac electrodes 305 electrically coupled to the patient's heart. The electrodes may be disposed implantably at multiple locations within, on, or about the heart, may be disposed subcutaneously, e.g., on the surface of an implantable device housing, and/or may be arranged patient-externally on the surface of the patient's skin, for example. In certain implementations, the electrodes 305 are coupled to switch matrix 325 circuitry used to selectively couple electrodes 305 to sense circuitry 310 and/or the pulse generator circuitry 330.

In various embodiments, the system 300 acquires and stores cardiac signals sensed via the electrodes 305 continuously or during a time window before, during, and/or after cardiac episodes. In some embodiments, the system 300 may additionally include sensors 365 other than the cardiac electrodes 305 and sensing circuitry 310. Signals sensed via the additional sensors 365 may be acquired and stored along with the cardiac signals. In one example, cardiac signals from each cardiac episode experienced by the patient are acquired along with one or more of cardiac marker channel signals, respiration signals sensed via a transthoracic impedance sensor, activity signals sensed via an accelerometer, a hemodynamic signals sensed via a pressure transducer, and/or other signals indicative of the patient status associated with the cardiac episode. The cardiac and other signals associated with the episode are stored in the memory 345 and may be time and date stamped.

In one implementation, the cardiac electrodes 305, sense circuitry 310, memory 345, and control processor 340 are components of an ICD. In this implementation, the episode data collected during one or more cardiac episodes may be transferred to the memory of a patient-external device 355 to facilitate interaction with a human analyst. For example, the implantable device may include communications circuitry 350 configured to transfer the stored episode data to the patient-external device 355 automatically, periodically, or on command. In addition, data and/or program commands useful for controlling the operation of various components of the ICD may be transmitted via the patient external device 355 and communications circuitry 350 and stored in the memory 345.

Figure 4:
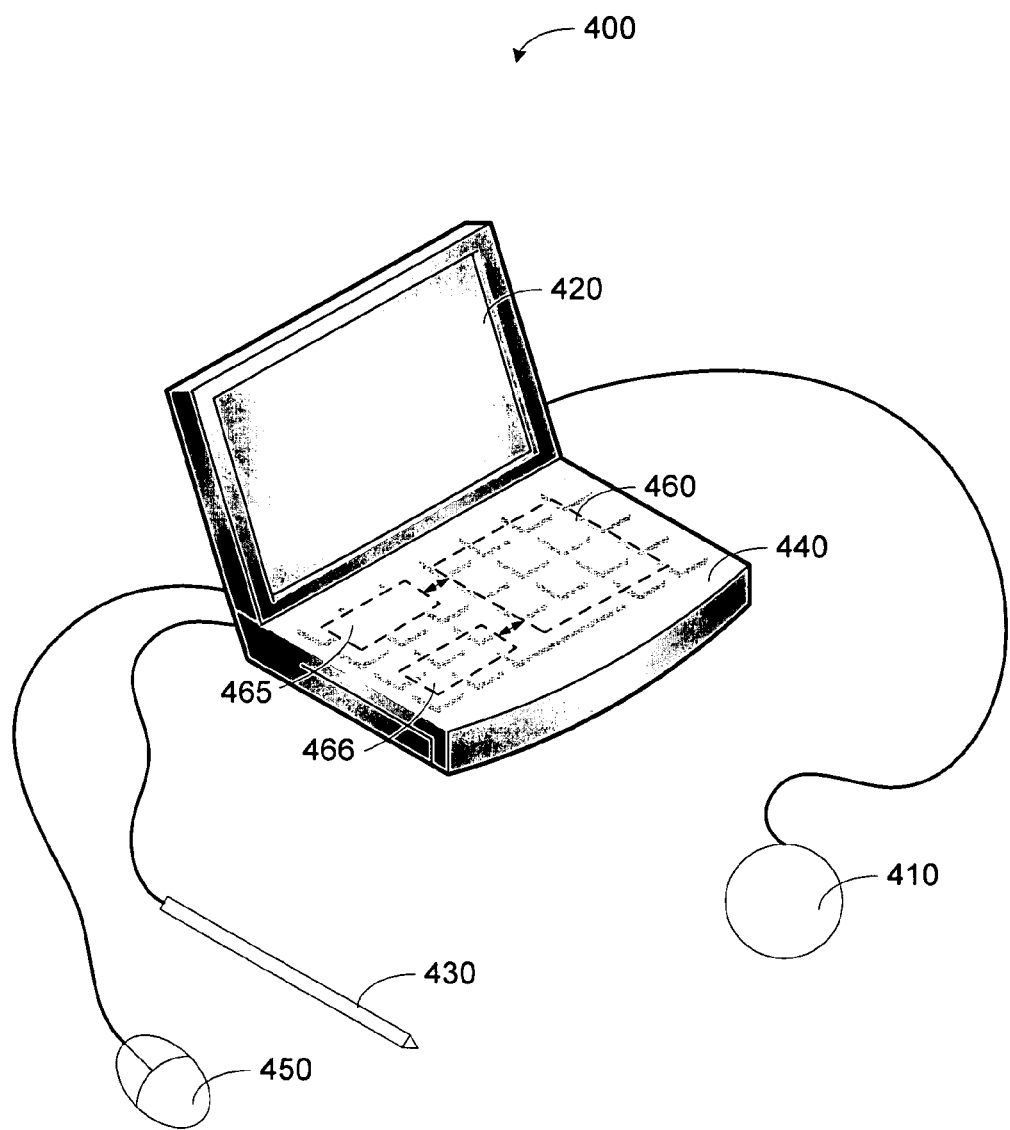
FIG. 4 is a diagram illustrating a patient-external device that provides a user interface allowing a human analyst to interact with the cardiac episode data in accordance with embodiments of the invention.

FIG. 4 illustrates a patient-external device 400 that provides a user interface allowing a human analyst to interact with the episode data. The patient-external device 400 is described as an ICD programmer, although the methods of the invention are operable on other types of devices as well, such as computers used in conjunction with an advanced patient management (APM) system, for example. The programmer 400 includes a programming head 410 which is placed over a patient's body near the implant site of an implanted device to establish a telemetry link between an ICD and the programmer 400. The telemetry link allows the cardiac episode data collected by the implantable device to be downloaded to the programmer 400. The downloaded cardiac episode data is stored in the programmer memory.

The programmer 400 includes a graphics display screen 420, e.g., LCD display screen, that is capable of displaying graphics, alphanumeric symbols, and/or other information on the display screen 420. For example, the programmer 400 may graphically display one or more of the cardiac signals downloaded from the ICD on the screen 420. The display screen 420 may include touch-sensitive capability so that the user can input information or commands by touching the display screen 420 with a stylus 430 or the user's finger. Alternatively, or additionally, the user may input information or commands via a keyboard 440 or mouse 450.

The programmer 400 includes a data processor 460 including software and/or hardware for managing cardiac episode data stored in the memory 465 of the programmer 400. In one implementation, cardiac episode data is received from an ICD via communications circuitry 466 of the programmer 400. The data processor 460 arranges the cardiac episodes based on one or more discriminating features of the cardiac episode data. The programmer 400 presents at least one selected episode to the user via that display screen 420. In one embodiment, presentation of the selected episode may include depicting a graphical representation of one or more cardiac signals of the episode, a portion of the episode, or one beat of the episode, on the display. Additional data, such as data acquired by various physiological or non-physiological sensors may be presented on the display 420, in some form, e.g., graphics or text, along with the cardiac signals. The user enters a label for the episode via an input device 430, 440, 450. The data processor appends the label to the data of the displayed episode and other episodes, e.g., episodes similar to the displayed episode.

In one embodiment, the programmer 400 displays cardiac signals and/or other data associated with an entire cardiac episode via the display screen 420. The user may observe the displayed signals and/or data and enter a label to be associated with the episode. For example, if the user determines that the cardiac signals are representative of SVT, the user may enter the label SVT-1 or other suitable label via the keyboard 440, the mouse 450, or stylus 430 for touch sensitive display applications.

The data processor 460 appends the label to the episode data stored in the memory 465 for that episode. The data processor 460 searches for additional episodes with discriminating features similar to the displayed episode. If episodes having similar discriminating features are found in memory, the data processor appends the label to the data of similar episodes. The episodes may be ordered or grouped based on the discriminating features.

The discriminating features used in various embodiments may be identified by the user or may be identified by the data processor 460, for example.

The above-described processes provide exemplary implementations that are particularly advantageous for forming morphology templates used for classifying various types of arrhythmia. For example, the user may enter a command to the programmer that episode beats having a certain label are to be used to form a template. The programmer forms the template from the identified episode beats and the template is uploaded to the ICD. The ICD uses the uploaded template to discriminate between episodes having cardiac signal morphologies similar to or dissimilar to the template morphology.

In one example, the ICD may deliver an appropriate tiered therapy based on identification of cardiac rhythms using the uploaded templates. For example, the ICD may deliver one or more of anti-tachyarrhythmia pacing, cardioversion or defibrillation based on the type of rhythm identified.

Figure 5:
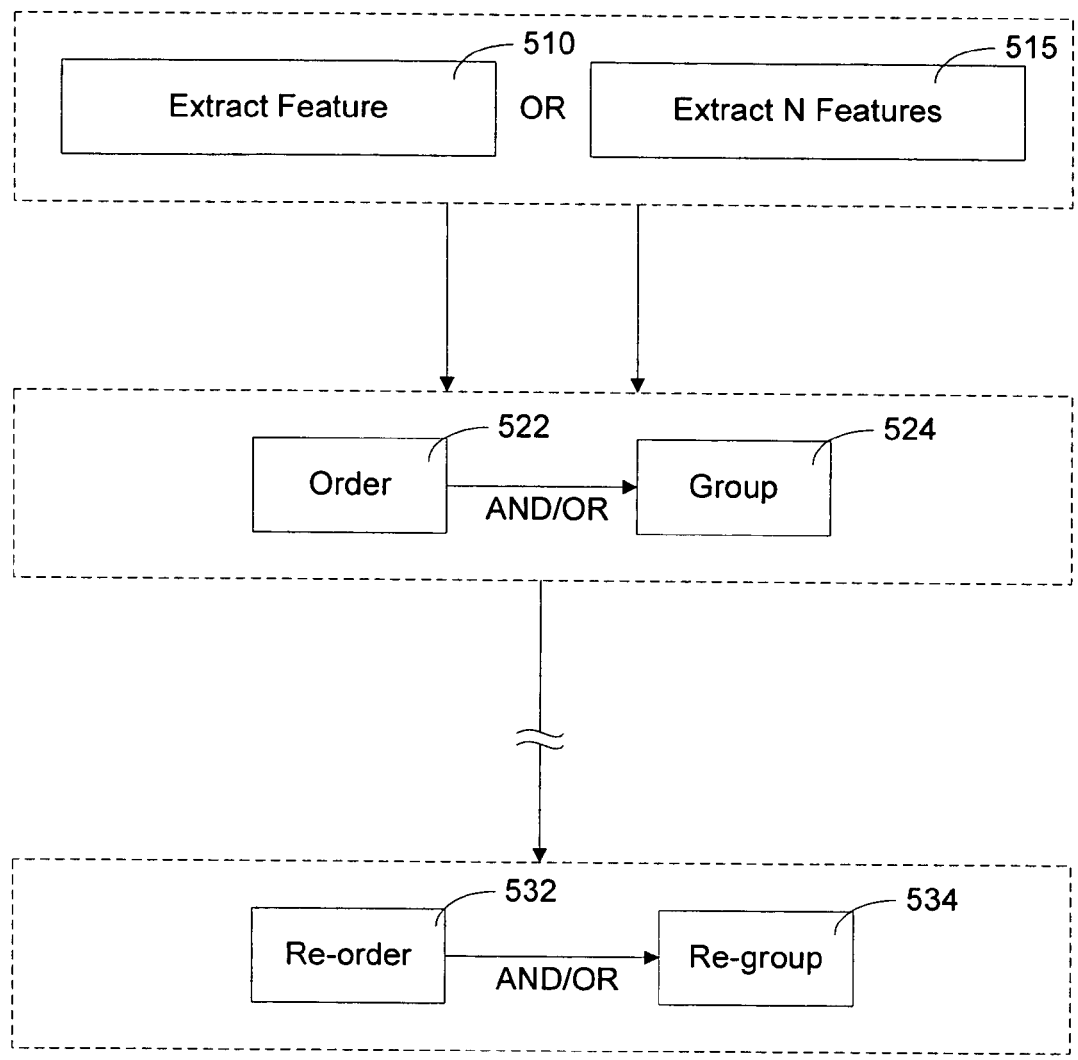
FIG. 5 is a flowchart that illustrates processes for arranging and labeling cardiac episodes in accordance with embodiments of the invention.

The flowchart of FIG. 5 illustrates processes for arranging and labeling cardiac episode data in accordance with embodiments of the invention. One or more discriminating features are selected. For example, the discriminating features may be features of cardiac signals that characterize the type of conduction pattern of an episode. The cardiac signals can include intracardiac electrogram (EGM) signals, subcutaneous small vector electrocardiogram (ECG) signals, and/or other types of cardiac signals, form example. In one implementation, one discriminating feature is extracted 510 from each episode's data. In other implementations, multiple discriminating features may be extracted 515.

For example, the discriminating feature(s) may involve binary information, such as when a particular episode either has or does not have the discriminating feature(s). The discriminating feature(s) may involve analog information, such as when the feature(s) are present in the episodes in varying amounts.

The episodes may be ordered 522 and/or grouped 524 based on their discriminating feature(s). In some embodiments, the episodes are ordered 522 based on their discriminating features but not grouped 524. In some embodiments, the episodes are grouped 524 but not ordered 522. In other embodiments, the episodes are ordered 522 and grouped 524. Grouping and/or ordering the episodes may be performed algorithmically. After the episodes are algorithmically grouped and/or ordered, a physician may override the algorithmic grouping and/or ordering and substitute a difference grouping and/or ordering.

In a simple case, the episodes may be grouped 524 into two groups based on whether the episodes have or do not have a particular discriminating feature. In some embodiments, the episodes may be ordered 522 based on their discriminating feature(s). For example, the episodes may be ordered 522 according to an analog value of a discriminating feature which is present in the episodes in varying amounts. In one scenario, the episodes are ordered 522 from the episode having the highest value of the discriminating feature to the episode having the lowest value of the feature.

In one scenario, the episodes are ordered 522 and/or grouped 524 according to a single discriminating feature of the episodes. In one example, the single discriminating feature may be the level or morphological organization associated with the episode data. The episodes may be ordered 522 and/or grouped 524 based on the morphological organization of the cardiac signals of the episode. Methods and systems for determining the morphological organization of episodes is described in commonly owned U.S. Pat. No. 7,908,001 which is incorporated herein by reference.

In another example, the single discriminating feature may be the angle of projection of the cardiac signal obtained using from ECG (non-local) signals associated with the episodes. Determination of the angle of projection of a cardiac signal is described in more detail in commonly owned U.S. Pat. No. 7,890,159 which is incorporated herein by reference.

A sensed ECG signal is effectively a superposition of all the depolarizations occurring within the heart that are associated with cardiac contraction, along with noise components. The propagation of the depolarizations through the heart may be referred to as a depolarization wavefront. The sequence of depolarization wavefront propagation through the chambers of the heart, providing the sequential timing of the heart's pumping, is designated an activation sequence.

A signal separation algorithm may be implemented to separate activation sequence components of ECG signals, and produce one or more cardiac signal vectors associated with all or a portion of one or more cardiac activation sequences based on the separation. The activation sequence components may be considered as the signal sources that make up the ECG signals, and the signal separation process may be referred to as a source separation process or simply source separation. One illustrative signal source separation methodology useful for producing cardiac signal vectors associated with cardiac activation sequences is designated blind source separation (BSS). Separation of cardiac signals using a BSS technique are described in commonly owned U.S. Pat. No. 7,706,866 which is incorporated herein by reference.

Selection of a vector involves multiple concurrent measurements obtained between multiple respective electrode pairs, chosen from at least three electrodes. After filtering, a cross-correlation matrix for the cardiac signals is computed, which may be averaged over a relatively short time interval, such as about 1 second. This process enhances the components that are mutually correlated. Eigenvalues of the cross-correlation matrix are computed. The smaller eigenvalues, normally associated with noise, may then be used to eliminate noise, by removing the noise components of the composite signals associated with those eigenvalues.

In general, the quality of the cardiac signal sensed from one pair of electrodes of a cardiac device depends on the orientation of the electrodes with respect to the depolarization wavefront produced by the heart. The signal sensed on an electrode bi-pole is the projection of the ECG vector in the direction of the bi-pole. The ECG or cardiac vector is most easily understood with reference to FIG. 7, described below. Algorithms of the present invention may advantageously exploit the strong correlation of signals from a common origin (the heart) across spatially distributed electrodes.

Figure 6:
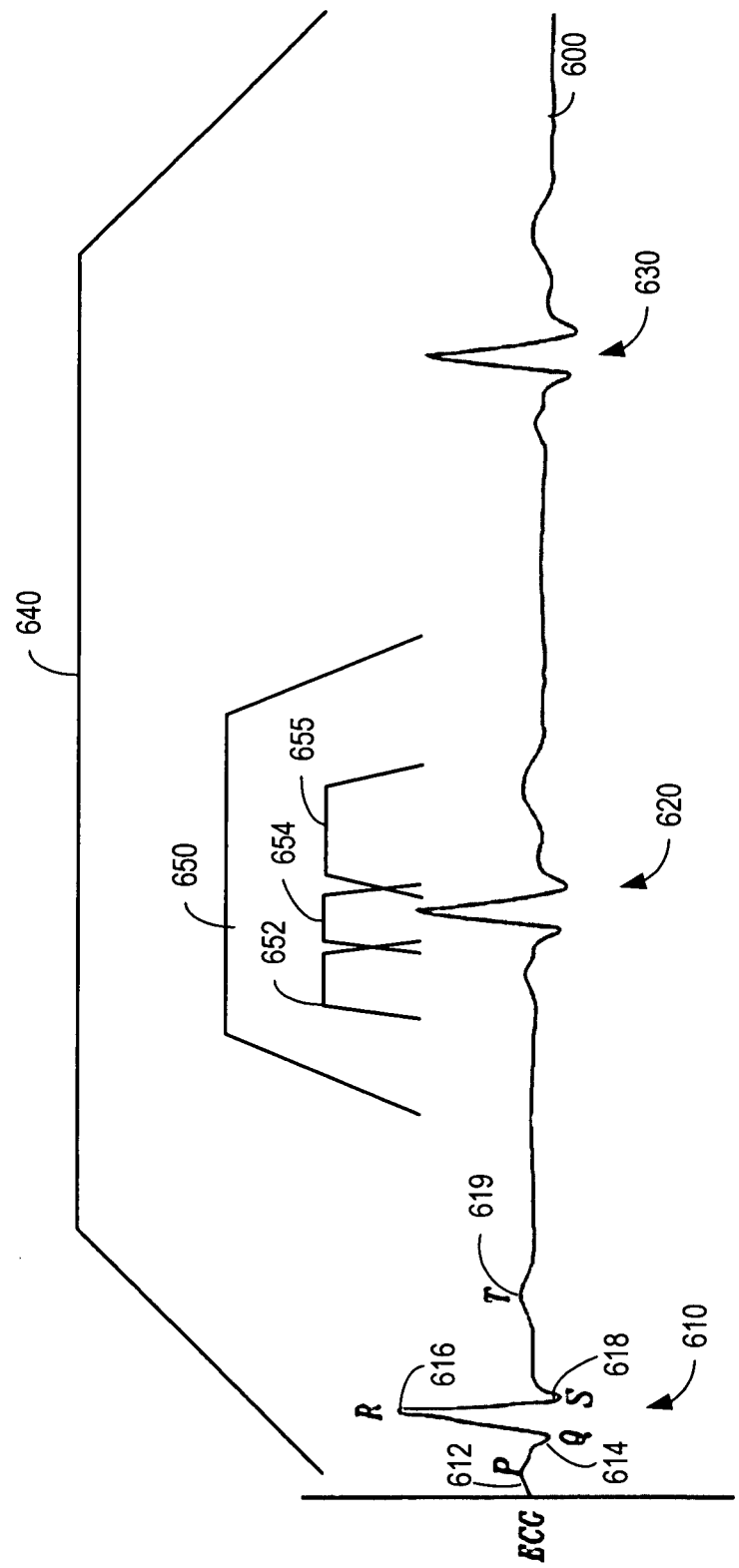
FIG. 6 is a graph illustrating three consecutive beats of a cardiac episode.

FIG. 6 illustrates a sensed ECG waveform 600 which is shown to have first, second, and third cardiac cycles 610, 620, 630, respectively. The P, Q, R, S, and T waves of the first cardiac cycle 610 are identified in the figure with reference numerals 612, 614, 616, 618, and 619, respectively. The ECG waveform 600 may be obtained directly or may be obtained indirectly, such as by using a signal separation methodology. Signal separation methodologies, such as BSS, are able to separate signals from individual sources that are mixed together into a composite signal. The main principle of signal separation works on the premise that spatially distributed electrodes collect components of a signal from a common origin (e.g., the heart) with the result that these components may be strongly correlated to each other. In addition, these components may also be weakly correlated to components of another origin (e.g., noise). A signal separation algorithm may be implemented to separate these components according to their sources and produce one or more cardiac signal vectors associated with all or a portion of one or more cardiac activation sequences based on the source separation.

Figure 7:
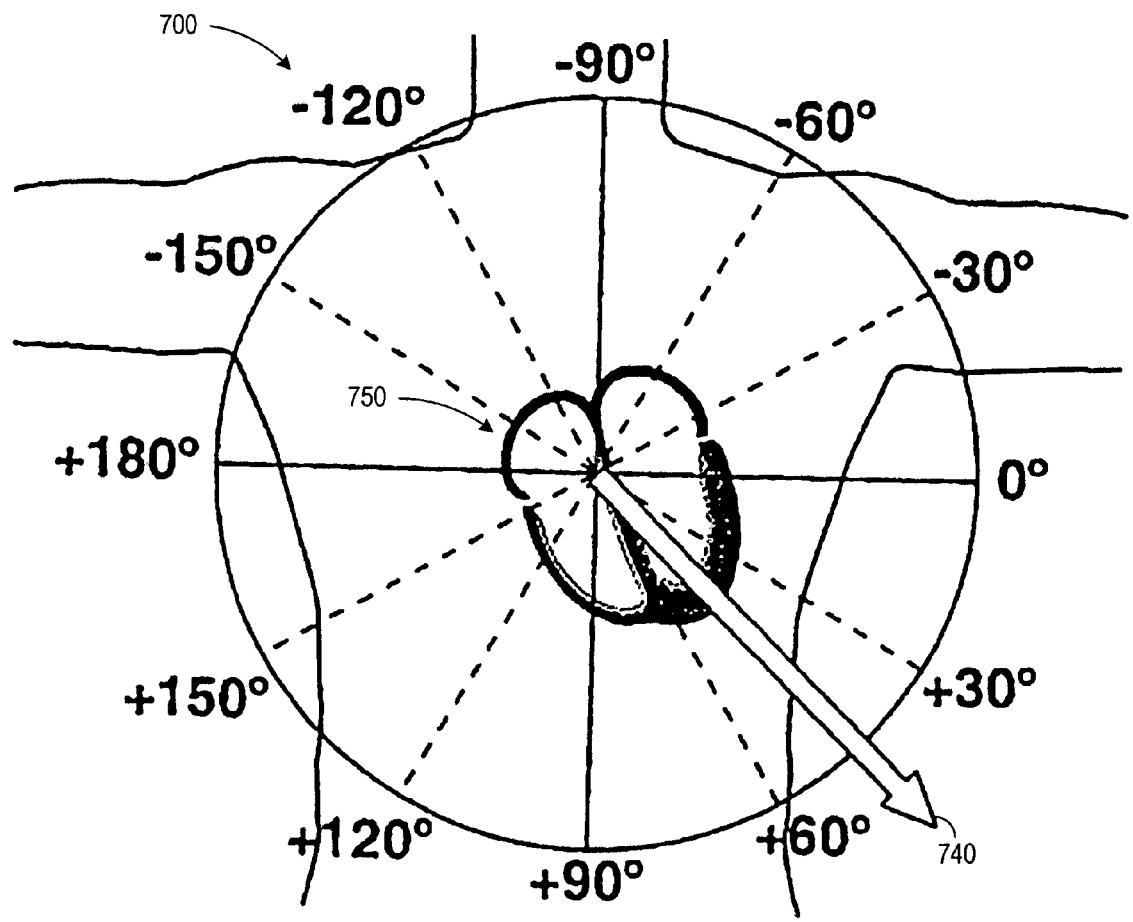
FIG. 7 is a polar plot of a cardiac vector superimposed over a frontal view of a thorax, with the origin of the polar plot located at the AV node of a patient's heart.

FIG. 7 illustrates a convenient reference for describing cardiac signal vectors associated with a depolarization wavefront. FIG. 7 is a polar plot 700 of a cardiac vector 740 superimposed over a frontal view of a thorax, with the origin of the polar plot located at a patient's heart 750, specifically, the atrioventricular (AV) node of the heart 750. The cardiac vector 740 is describable as having an angle, in degrees, about a circle of the polar plot 700, and having a magnitude, illustrated as a distance from the origin of the tip of the cardiac vector 740. The polar plot 700 is divided into halves by a horizontal line indicating 0 degrees on the patient's left, and +/−180 degrees on the patient's right, and further divided into quadrants by a vertical line indicated by −90 degrees at the patient's head and +90 degrees on the bottom. The cardiac vector 740 is projectable onto the two-dimensional plane designated by the polar plot 700.

The cardiac vector 740 is a measure of all or a portion of the projection of a heart's activation sequence onto the polar plot 700. The cardiac vector 740 may be, for example, associated with the entire cardiac cycle, and describe the mean magnitude and mean angle of the cardiac cycle.

Figure 8:
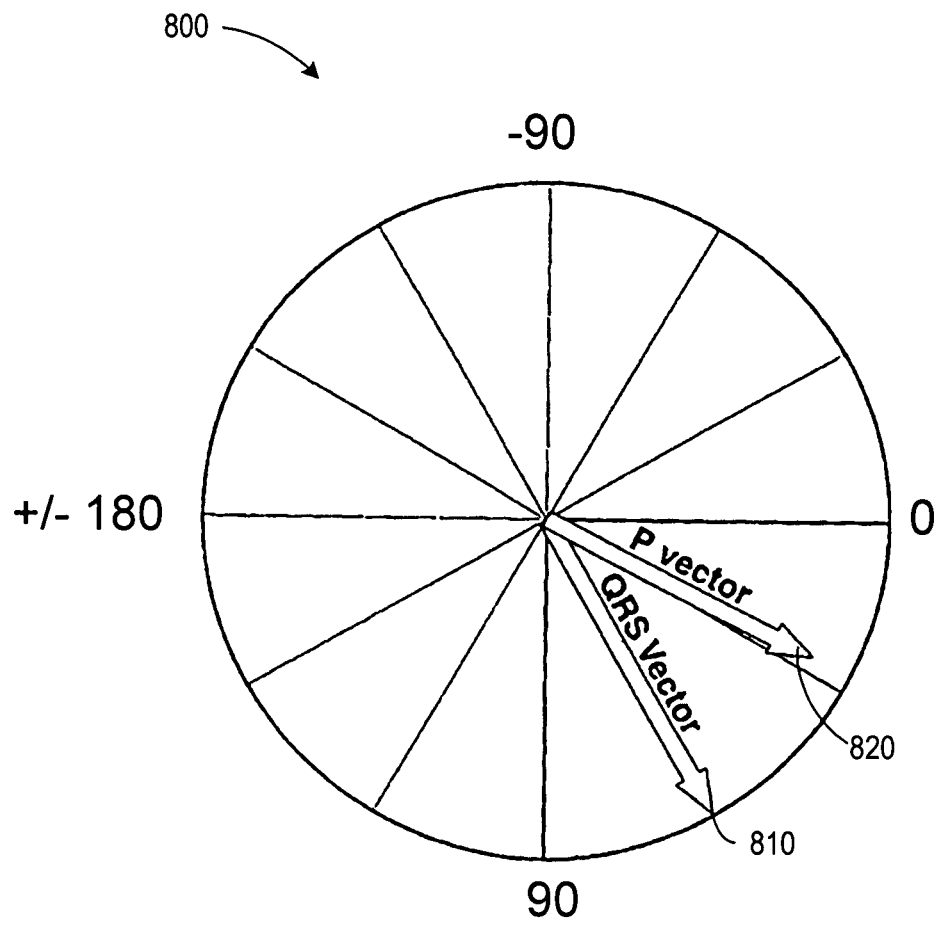
FIG. 8 is a polar plot of cardiac vectors obtained using a source separation in accordance with the present invention.

Referring now to FIG. 8A, a polar plot 800 is illustrates separate portions of the cardiac cycle that may make up the cardiac vector 740 of FIG. 7. As is illustrated in FIG. 8, a QRS vector 810 and a P vector 820 are illustrated having approximately 60 degree and 30 degree angles, respectively.

The QRS vector 810 represents the projection of the mean magnitude and angle of the depolarization wavefront during the QRS portion of the cardiac cycle onto the polar plot 800. The P vector 820 represents the projection of the mean magnitude and angle of the depolarization wavefront during the P portion of the cardiac cycle onto the polar plot 800. The projection of any portion of the depolarization wavefront may be represented as a vector (angle and magnitude) on the polar plot 800.

Further, any number of cardiac cycles may be combined to provide a statistical sample that may be represented by a vector as a projection onto the polar plot 800. Likewise, portions of the cardiac cycle over multiple cardiac cycles may also be combined, such as combining a weighted summation of only the P portion of the cardiac cycle over multiple cardiac cycles, for example.

Referring now to FIGS. 6 through 8, the first, second, and third cardiac cycles 610, 620, and 630 may be analyzed using a window 640 (FIG. 6) applied concurrently to signals sensed by three or more cardiac sense electrodes. The ECG waveform signals 600 from all the sense electrodes, during the window 640, may be provided to a signal processor. The signal processor may then perform a source separation that provides the cardiac vector 740 (FIG. 7). The cardiac vector 740 then represents the orientation and magnitude of the cardiac vector that is effectively an average over all three cardiac cycles 610, 620, and 630.

Other windows are also useful. For example, a window 650 and another window may provide each full cardiac cycle, such as the cardiac cycle 620 and the cardiac cycle 630 illustrated in FIG. 6, to a controller for analysis. Such windows may be useful for beat-to-beat analysis.

Examples of other useful windows include a P-window 652, a QRS window 654, and an ST window 655 (FIG. 6) that provide within-beat vector analysis capability, such as by providing the P-vector 820 and the QRS-vector 810 illustrated in FIG. 8.

As previously stated, the angle of the cardiac signal vector for a cardiac cycle, or portion thereof, may comprise a single discriminating feature used for arranging the cardiac episodes. In various implementations, the cardiac episodes may be ordered and/or grouped based on the angle of the cardiac signal vector.

Returning now to FIG. 5, in one embodiment, the episodes may be ordered 522 and/or grouped 524 according to a linear or non-linear combination of N discriminating features. For example, the N discriminating features may be extracted from cardiac signals of the episode. In one embodiment, the N discriminating features are extracted from a composite waveform formed from multiple beats of an episode.

Figure 9:
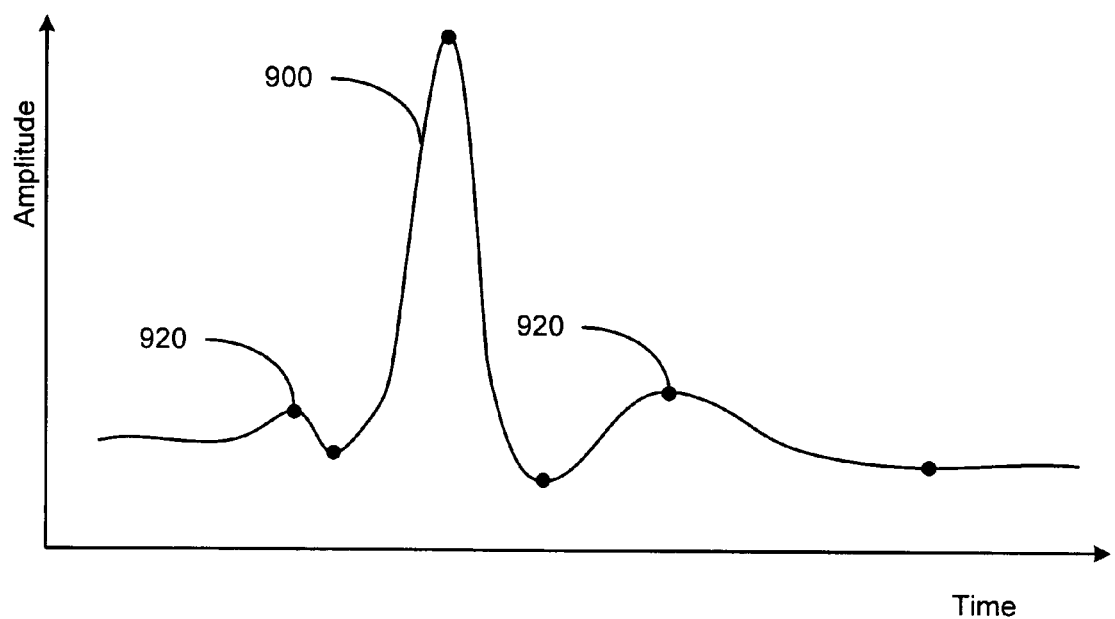
FIG. 9 shows an example of a composite cardiac beat signal of a cardiac episode.

FIG. 9 shows an example of a composite signal 900 of cardiac beat signals of a cardiac episode. The composite signal includes repeatably identifiable features 920 that may be used for discrimination between different types of arrhythmias, for example. The features extracted from the signal 900 may include the time coordinates of local maxima and minima points of the cardiac signal 900, for example. The features 920 may then used to create an "N" dimensional feature vector. In one embodiment, the feature vector has the form: $A=[A1, A2, A3 . . . An]$, where each of the values A1-An represent scalar values derived from the repeatably identifiable features of the composite beat signal for the episode. Additional details related to extraction of features points from cardiac signals and the use of such feature points to discriminate between various cardiac rhythms is described in commonly owned U.S. Pat. Nos. 6,266,554 and 6,449,503 which are incorporated herein by reference.

In yet another embodiment, the N discriminating features extracted from each episode are coefficients of Fourier or wavelet decomposition of a composite cardiac beat signal for the episode. In one implementation, the composite beat signal of an episode is transformed into a number of signal wavelet coefficients using a wavelet transform, such as a Haar wavelet transform. The N higher amplitude signal wavelet coefficients are identified and used as the N discriminating features of the episode. Additional details regarding the use of wavelet transformation to extract wavelet coefficients of cardiac signals is described in U.S. Pat. No. 6,393,316 which is incorporated herein by reference.

In yet a further embodiment, the N discriminating features of the episodes comprise areas between N sections of a composite cardiac beat signal and a baseline. For example, a group of M consecutive peaks having the largest cumulative peak values are determined from the composite signal. Features of the peaks such as areas of each peak, are determined and used as the N discriminating features of the composite cardiac beat signal of the episode. Additional features may comprise the polarity and/or position of the peak. Further discussion regarding the extraction of peak information as discriminating features of a cardiac signal are discussed in U.S. Pat. No. 5,779,645 which is incorporated herein by reference.

With reference to arranging and labeling tachyarrhythmic cardiac episodes, formation of a composite cardiac beat signal may involve calculating a sample-by-sample average of all cardiac beat signals in the episode that are identified as "fast" cardiac beats, e.g., beats that follow an R-R interval that is less than a predetermined value. Alternatively, the composite signal may be formed by calculating the sample-by-sample average of a predetermined number of beats of a tachyarrhythmia episode. For example, a predetermined number of beats at the end of the episode may be used. This implementation assumes that the last predetermined number of beats of the episode are tachyarrhythmic.

In some embodiments, the discriminating features are extracted from marker channels associated with the cardiac signals. For example, the discriminating features may include the P-P, P-R, R-P, or R-R timing intervals, atrial rate compared to ventricular rate the stability of the intervals and/or the onset characteristics of the intervals.

In some embodiments the discriminating features may include cardiac rate. For example, SVT episodes may be grouped according to rate. These SVT episode groups may be used to form rate-indexed templates. Formation and use of rate-indexed templates is further described in commonly owned U.S. patent application Ser. No. 11/312,280, filed Dec. 20, 2005 which is incorporated herein by reference.

In one embodiment, the discriminating features may comprise results of each of N rhythm discriminators used to discriminate, for example, between SVT and VT/VF. In another embodiment, a discriminating feature may comprise a validation metric preferably calculated by taking the individual probabilities of each of a number of arrhythmia discrimination and multiplying these probabilities to produce a combined probability. Determination of validation metrics for arrhythmia discrimination is further discussed in commonly owned U.S. Patent Application Ser. No. 60/844,253, filed Sep. 13, 2006 which is incorporated herein by reference.

As previously described, in some embodiments, the discriminating features can be extracted from signals other than the cardiac signals. For example, the discriminating features may include those extracted from hemodynamic signals, activity signals, posture signals, respiration signals and/or other physiological or non-physiological signals associated with the cardiac episode.

In yet other embodiments, the discriminating features can describe the patient status at the time the episode occurred, such as the patient's indications, demographics, pharmacologic treatment, and other status indicators.

The discriminating features used to arrange the episode data may be a combination of any of the features described herein or other features.

The patient's physician may choose which discriminating feature or features are used to arrange the cardiac episodes. The programmer may present a query window on the display to receive user-specified discriminating features, for example. In some embodiments, after arranging the cardiac episodes and/or appending the labels, the programmer displays only those episodes corresponding to the discriminating features specified by the user. In other embodiments, the programmer displays an ordered list of the episodes. Various implementations for identifying and displaying episode data is described in commonly owned U.S. Pat. Nos. 6,253,102 and 6,418,340 which are incorporated herein by reference.

Referring again to FIG. 5, as previously mentioned, in some embodiments, the episode data is ordered 522 but not grouped 524. For example, the episode data may be ordered 522 based on a numerical value of a discriminating feature, such as the angle of projection of the cardiac signals, described above. In other embodiments, the episode data is ordered 522 according to multiple discriminating features.

In one example, N features are extracted from a composite cardiac beat signal of the episode and are compared to N features of a template. A similarity measure is determined based on the comparison. For example, the template used for comparison may be representative of a particular type of rhythm, such as normal sinus rhythm (NSR), supraventricular tachyarrhythmia (SVT), or ventricular tachyarrhythmia (VT). The episodes may be arranged according to the similarity measure produced by the comparison between the composite waveforms of the episodes and the template. In some embodiments, the similarity measure between the composite cardiac beat signal and the template may be expressed as a correlation coefficient, for example.

Various methods for determining a template representative of a particular type of rhythm and/or for comparing the templates to the N features of a beat waveform are described in the following commonly owned patent documents which are incorporated herein by reference: U.S. Pat. Nos. 6,449,503, 6,708,058, 6,889,079, 7,085,599 and 7,894,893. Methods for determining similarity measures between templates and cardiac beat signals based on wavelet analysis and based on peak information are described in previously incorporated U.S. Pat. Nos. 6,393,316 and 5,779,645, respectively. Similarity measures determined via these techniques may be used for ordering 522 or grouping 524 the data in accordance with various approaches.

In another embodiment, the episodes are grouped 524 but are not necessarily ordered 522. For example, the episodes may be clustered using a genetic algorithm, such as a K-means clustering algorithm. In one embodiment involving K-means clustering, each episode's N distinguishing features are expressed as an N-dimensional feature vector. The feature vectors of all episodes are plotted in N-dimensional space. Episodes similar in conduction pattern will be plotted close to each other while episodes having different in conduction pattern will be plotted farther from each other. The K-means clustering algorithm will automatically cluster the episodes into K groups, with each group represented by its mean feature vector and each episode assigned to the group with the closest mean feature vector.

In some embodiments, groups may be formed where a particular episode can be a member of only one group. In other embodiments, a particular episode may be a member in more than one group. For example, a fuzzy K-means clustering algorithm may be used to group the episodes. With conventional K-means clustering described above, an episode can belong to only one cluster as the conventional algorithm assigns to an episode one crisp membership value per cluster (equal to 0 if the episode is not a member of the cluster and 1 if the episode is a member of the cluster). In contrast, with the fuzzy algorithm, an episode can belong to several clusters, as the fuzzy algorithm assigns to an episode one membership value per cluster ranging from 0 to 1. These membership values specify the episode's degree of membership into each cluster.

Note that in the above-described embodiments, the number of clusters is first determined before using the genetic K-means algorithm to cluster the episodes. In some implementations, the physician specifies K which is the number of groups or clusters. In other implementations, the processor uses a predetermined number as K. In yet other implementations, the processor determines the value of K by partitioning the N-dimensional space based upon the density of the feature vectors in the space. In a further implementation, the processor determines the value of K by partitioning the N-dimensional space based upon a matrix of similarity measurements comparing each feature vector to each other.

In one scenario, the processor may use a probability function such as a probability density function (PDF) or a cumulative distribution function (CDF) to determine the number of clusters. This technique is described with reference to determining the number of rate zones in commonly owned U.S. Pat. No. 7,580,741 which is incorporated herein by reference. The same principle is applicable to determining the number of clusters based on the PDF or CDF formed using discriminating features or mean feature vectors of the episodes. The number of groups may be determined from the morphology of the CDF or PDF as is described for determining the number of rate zones in the previously incorporated patent application.

In yet other embodiments, the episodes are first ordered 522 and are then grouped 524. For example, the episodes may first be ordered 522 based on the value of one discriminating feature or may be ordered based on N discriminating features as described above. A physician or algorithm may identify groups of the ordered episodes. In one scenario, the physician may identify episodes, denoted herein as border episodes. The border episodes may have one or more discriminating features that appear to form a natural division between one group and another group, for example.

In another scenario, an algorithm determines the border episodes. If the episode groups or boundary episodes are algorithmically determined, the physician may have the opportunity to override these algorithmic determinations and substitute different episode groupings or boundary episodes.

Figure 10:
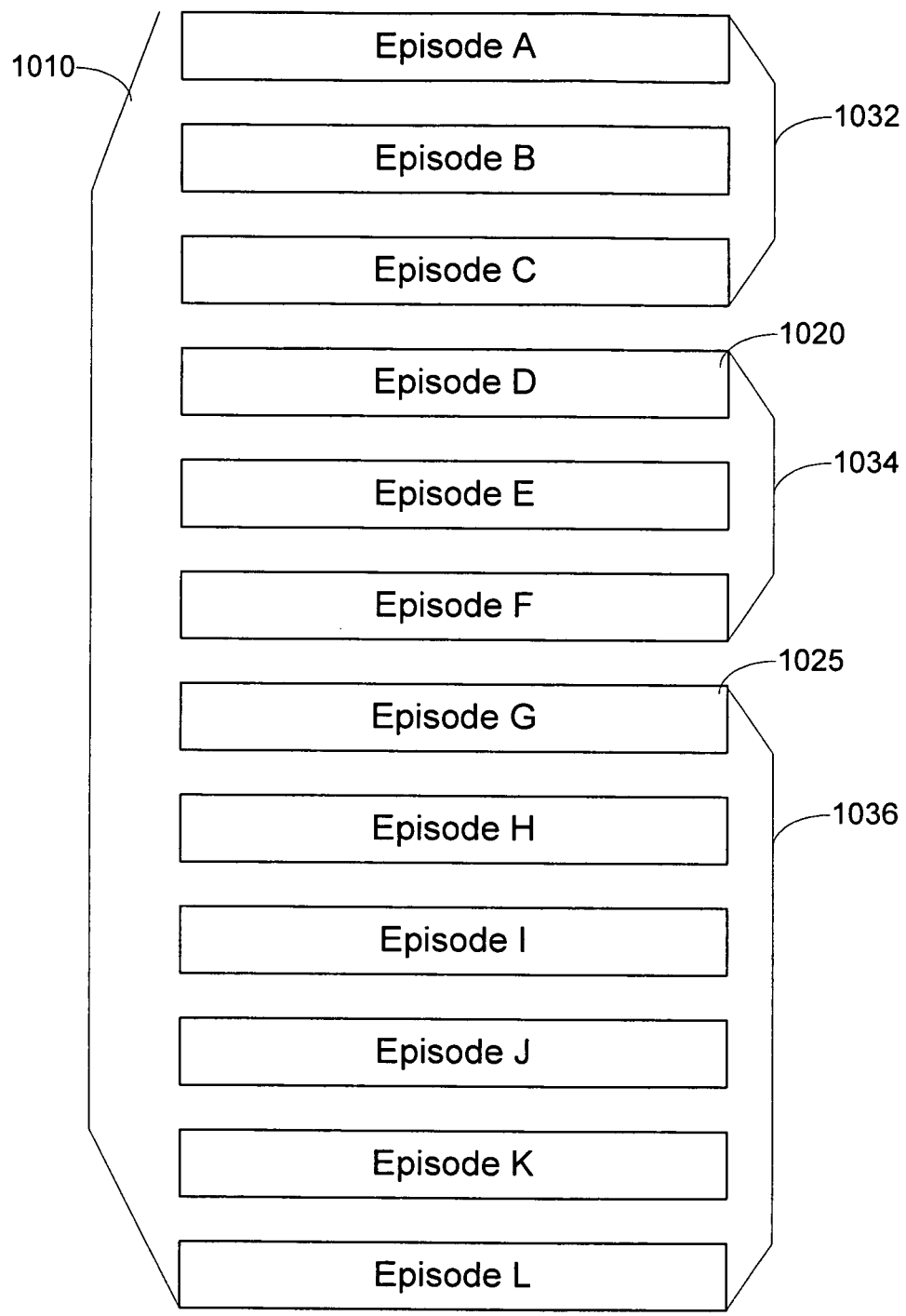
FIG. 10 pictorially illustrates grouping ordered episodes using border episodes in accordance with embodiments of the invention.

FIG. 10 illustrates grouping using border cases identified by the physician. The episodes A-L are illustrated in an ordered arrangement 1010. The physician interacts with the user interface of the programmer, for example, to identify the border cases 1020, 1025 to the data processor of the programmer. The data processor uses the border cases 1020, 1025 to group the episodes A-C, D-F, G-L into groups 1032, 1034, 1036, respectively, using the border cases 1020, 1025. In one embodiment, the Support Vector Machine (SVM) algorithm is used to group the ordered episodes using the physician annotated border cases as the support vectors.

Returning to FIG. 5, after a first process of arranging and algorithmically appending the episode label or labels, the episodes may be subsequently re-arranged, for example by re-ordering 532, and/or re-grouping 534. New cardiac episode data may be acquired and new episodes inserted into a previously determined order or into previously formed groups, or to be used to form new groups. Rearrangement of the episodes may be triggered automatically at regular intervals or may be triggered at irregular intervals such as when the patient experiences a cardiac episode, e.g., a tachyarrhythmia episode. Alternatively, rearrangement may be triggered manually by a physician, for example, during a follow-up visit or remotely through an advanced patient management system.

As the amount of information collected and stored in ICDs increases, the interpretation of data becomes more complex and time consuming. The present invention provides methods and systems for arranging cardiac episodes based on discriminating features of the episode data. The processes described herein allow a physician to more easily identify and label cardiac episodes and/or cardiac beats having similar features. The episodes may be automatically ordered and/or grouped to facilitate formation of NSR, SVT and/or VT templates and to provide enhanced confidence that the rhythms used in template formation represent recurring arrhythmia types. The ordered and/or grouped episodes may be used by the physician to identify the number and/or frequency of different types of cardiac episodes experienced by the patient. Data processing algorithms used to arrange and/or label the episodes may operate in an implantable or patient-external device that also acquires the episode data. In another version, an implantable or non-implantable device may acquire the episode data and the arrangement and/or labeling of the data may be performed by a device programmer or a remote server, for example.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method operable on data acquired by an implantable cardiac device and associated with a plurality of cardiac episodes, the method comprising:
   algorithmically grouping, with at least one of a number of data processors, the cardiac episodes based on multiple discriminating features of the episodes, each cardiac episode including a plurality of consecutive cardiac beats, wherein the discriminating features include at least one feature from a cardiac signal and at least one feature from a non-cardiac signal;
   algorithmically selecting, with at least one of the number of data processors, at least one episode from an arrangement of cardiac episodes;
   graphically displaying an electrogram (EGM) signal of the at least one episode to a user through a patient-external user interface;
   after displaying the EGM signal, receiving an input from a user through the patient-external user interface, the input from the user identifying a user-selected label that characterizes the EGM signal of the selected episode;
   algorithmically appending, with at least one of the number of data processors, the user-selected label to data of the selected episode; and
   algorithmically appending, with at least one of the number of data processors, the user-selected label to data of non-selected episodes of the arrangement of cardiac episodes.

2. The method of claim 1, wherein grouping the cardiac episodes comprises grouping the episodes based on similarity of the one or more discriminating features.

3. The method of claim 1, wherein a number of groups is determined by a user.

4. The method of claim 1, wherein a number of groups is determined algorithmically.

5. The method of claim 1, wherein grouping the cardiac episodes comprises ordering the episodes based on the one or more discriminating features and grouping the ordered episodes.

6. The method of claim 5, wherein grouping the ordered episodes comprises:
   identifying, by the user, one or more ordered episodes defining boundary episodes between groups; and
   algorithmically grouping, with at least one of the number of data processors, the ordered episodes based on the boundary episodes.

7. The method of claim 1, wherein receiving the input from the user comprises:
   algorithmically selecting, with at least one of the number of data processors, a label for the selected episode; and confirming, by the user, the algorithmically selected label or selecting, by the user, a label different from the algorithmically selected label.

8. The method of claim 1, further comprising receiving additional episode data acquired by the implantable cardiac device and repeating the algorithmically grouping and algorithmically appending processes using previously acquired episode data and the additional episode data.

9. The method of claim 8, wherein repeating the algorithmically grouping and algorithmically appending processes is initiated algorithmically or manually.

10. The method of claim 1, wherein the one or more discriminating features of the episodes characterize a conduction pattern of an arrhythmic episode or a type of arrhythmia.

11. The method of claim 1, wherein the label characterizes at least some of the cardiac episodes as tachyarrhythmia episodes that are ventricular in origin or supraventricular in origin.

12. The method of claim 1, wherein the label characterizes at least some of the cardiac episodes as tachyarrhythmia episodes that are hemodynamically stable or hemodynamically unstable.

13. The method of claim 1, wherein the label characterizes at least some of the arrhythmia episodes as tachyarrhythmia episodes that should be treated with anti-tachyarrhythmia therapy or those that should not be treated with anti-tachyarrhythmia therapy.

14. The method of claim 1, wherein at least one of algorithmically grouping, receiving the user-selected label, and algorithmically appending the label is implementable by the implantable cardiac device.

15. The method of claim 1, wherein at least one of algorithmically grouping, presenting the at least one episode to the user, receiving the user-selected label, and algorithmically appending is implemented by a processor external of the implantable cardiac device.

16. The method of claim 1, further comprising:
determining a morphological organization of the cardiac episodes; and
algorithmically grouping, with at least one of the number of data processors, the cardiac episodes based on the morphological organization of the cardiac episodes.

17. The method of claim 1, wherein algorithmically grouping, with at least one of the number of data processors, the cardiac episodes further comprises algorithmically grouping the cardiac episodes using a fuzzy clustering algorithm.

18. The method of claim 1, further comprising:
determining an angle of projection of the cardiac signal; and
algorithmically grouping, with at least one of the number of data processors, the cardiac episodes based on the angle of projection of the cardiac signal.

19. A system, comprising:
cardiac electrodes and sensing circuitry configured to acquire data associated with cardiac episodes, each cardiac episode including a plurality of consecutive cardiac beats;
a user interface configured to graphically display an electrogram (EGM) signal of a selected cardiac episode to a user and to subsequently receive an input from the user that identifies a user-selected label for the episode; and
a data processor configured to group the cardiac episode data based on multiple discriminating features of the episodes and to append the user-selected label to the data of the selected cardiac episode and to data of non-selected cardiac episodes having features that are similar to the discriminating feature, wherein the discriminating features include features from a cardiac signal and features from at least one non-cardiac signal.

20. The system of claim 19, further comprising at least one sensor other than the cardiac electrodes, the at least one sensor configured to acquire physiological or non-physiological data associated with the cardiac episodes.

21. The system of claim 19, wherein at least one of the cardiac electrodes and sensing circuitry and data processor are components of an implantable cardiac device.

22. The system of claim 19, wherein:
the cardiac electrodes and sensing circuitry are components of an implantable device; and
the user interface and data processor are components of a non-implantable device.

23. The system of claim 19, wherein the cardiac episodes are tachyarrhythmia episodes.

24. The system of claim 19, wherein the labeled episode data is used to form a morphology template for discriminating cardiac rhythms.

25. The system of claim 19, wherein grouping the cardiac episode data comprises ordering the cardiac episode data and grouping the ordered episodes.

26. A system comprising:
a number of data processors for:
algorithmically grouping cardiac episodes based on one or more discriminating features of the episodes, each cardiac episode including a plurality of consecutive cardiac beats, wherein the discriminating features include features from a cardiac signal and features from at least one non-cardiac signal;
algorithmically selecting at least one episode from an arrangement of cardiac episodes;
graphically displaying an electrogram (EGM) signal of at least one episode to a user through a patient-external user interface;
receiving, after the EGM signal of the at least one selected episode is displayed, an input from a user through the patient-external user interface, the input from the user identifying a user-selected label that characterizes the EGM signal of the at least one selected episode;
algorithmically appending the user-selected label to data of the at least one selected episode; and
algorithmically appending the user-selected label to data of non-selected episodes of the arrangement of cardiac episodes.

27. The system of claim 26, further comprising grouping the episodes based on similarity of the one or more discriminating features.

28. The system of claim 26, further comprising ordering the episodes based on the one or more discriminating features.

* * * * *